US012721895B2

(12) United States Patent
Nishikawa et al.

(10) Patent No.: US 12,721,895 B2
(45) Date of Patent: Sep. 1, 2026

(54) SURFACE-MODIFIED NANOPARTICLE

(71) Applicants: KYOTO UNIVERSITY, Kyoto (JP); DAICEL CORPORATION, Osaka (JP)

(72) Inventors: Masahiro Nishikawa, Tokyo (JP); Naoki Komatsu, Kyoto (JP)

(73) Assignees: KYOTO UNIVERSITY, Kyoto (JP); DAICEL CORPORATION, Osaka (JP)

( * ) Notice: Subject to any disclaimer, the term of this patent is extended or adjusted under 35 U.S.C. 154(b) by 334 days.

(21) Appl. No.: 18/566,888

(22) PCT Filed: Jun. 9, 2022

(86) PCT No.: PCT/JP2022/023332
§ 371 (c)(1),
(2) Date: Dec. 4, 2023

(87) PCT Pub. No.: WO2022/260136
PCT Pub. Date: Dec. 15, 2022

(65) Prior Publication Data

US 2024/0277848 A1 Aug. 22, 2024

(30) Foreign Application Priority Data

Jun. 11, 2021 (JP) ................................ 2021-098083

(51) Int. Cl.
*A61K 41/00* (2020.01)
*A61K 47/60* (2017.01)
*A61K 47/69* (2017.01)

(52) U.S. Cl.
CPC .......... *A61K 41/0095* (2013.01); *A61K 47/60* (2017.08); *A61K 47/6923* (2017.08)

(58) Field of Classification Search
CPC ................ A61K 41/0095; A61K 47/60; A61K 47/6923; A61K 47/6935; A61K 33/22; C01B 32/28; B82Y 30/00; A61P 35/00
See application file for complete search history.

(56) References Cited

FOREIGN PATENT DOCUMENTS

| | | |
|---|---|---|
| CN | 103043647 A | 4/2013 |
| CN | 103877940 A | 6/2014 |
| CN | 110812490 A | 2/2020 |
| JP | 2009-51766 A | 3/2009 |
| JP | 2015-147733 A | 8/2015 |

OTHER PUBLICATIONS

Extended European Search Report for European Application No. 22820315.4, dated Mar. 19, 2026.
Feiner et al., "Pre-targeting with ultra-small nanoparticles: boron carbon dots as drug candidates for boron neutron capture therapy," Journal of Materials Chemistry B, vol. 9, No. 2, 2021, pp. 410-420.
Nishikawa et al., "Conjugation of Phenylboronic Acid Moiety through Multistep Organic Transformations on Nanodiamond Surface for an Anticancer Nanodrug for Boron Neutron Capture Therapy," Bulletin of the Chemical Society of Japan, vol. 94, No. 9, Sep. 15, 2021, pp. 2302-2312.
Beyranvand et al., "Boronic acid functionalized graphene platforms for diabetic wound healing," Carbon, vol. 158, 2019, pp. 327-336.
International Preliminary Report on Patentability and Written Opinion of the International Searching Authority for International Application No. PCT/JP2022/023332, dated Nov. 21, 2023, with an English translation.
International Search Report for International Application No. PCT/JP2022/023332, dated Aug. 23, 2022, with English translation.
Nomoto et al., "Poly(vinyl alcohol) boosting therapeutic potential of p-boronophenylalanine in neutron capture therapy by modulating metabolism," Science Advances, vol. 6, No. 4, Jan. 22, 2020, 12 pages total.
Zhong et al., "A Reusable Interface Constructed by 3-Aminophenylboronic Acid Functionalized Multiwalled Carbon Nanotubes for Cell Capture, Release, and Cytosensing," Advanced Functional Materials, vol. 20, 2010, pp. 992-999.
Chinese Office Action and Search Report for Chinese Application No. 202280040669.6, dated Jul. 31, 2025.

*Primary Examiner* — Kamal A Saeed
*Assistant Examiner* — Meghan C Heasley
(74) *Attorney, Agent, or Firm* — Birch, Stewart, Kolasch & Birch, LLP

(57) ABSTRACT

Provided are a surface-modified nanoparticle that can be easily produced and can selectively deliver boron atoms into cancer cells and maintain the boron atoms, and a method for producing the surface-modified nanoparticle. The surface-modified nanoparticle of the present disclosure includes a nanocarbon material, and a surface-modifying group of the nanocarbon material, and has a group containing a boron atom as the surface-modifying group.

15 Claims, 23 Drawing Sheets

SURFACE-MODIFIED NANOPARTICLE

TECHNICAL FIELD

The invention according to the present disclosure relates to a surface-modified nanoparticle. The present application claims priority to Japanese Patent Application Number 2021-098083 filed in Japan on Jun. 11, 2021, the content of which is incorporated herein by reference.

BACKGROUND ART

Boron neutron capture therapy (BNCT) destroys cancer cells by using alpha rays ($^{4}$He nuclei) and lithium nuclei ($^{7}$Li nuclei) emitted by the nuclear reaction between boron ($^{10}$B) and neutrons and is one type of advanced cancer therapy. The movable distances of the α-ray and the $^{7}$Li nucleus generated by the nuclear reaction are approximately several microns, respectively, which is approximately the same as the cell size. For this reason, selective and sufficient accumulation of boron (a boron compound) in cancer tissues and/or cancer cells would enable cancer cells to be selectively killed.

Currently, p-boronophenylalanine (BPA) is used in clinical applications as a boron drug used in BNCT (Patent Document 1). BPA is known to be taken up into a cancer cell via an L-amino acid transporter (LAT-1) expressed on the surface of the cancer cell. However, penetration of BPA through the cell membrane (cellular uptake and excretion) via LAT-1 is reversible, and BPA is rapidly metabolized (excreted) due to being a low molecular weight compound. Thus, to maintain the BPA concentration in a cancer cell during neutron irradiation, it desirable to increase extracellular BPA concentration. That is, in BNCT, continuous administration of high-concentration BPA is desirable.

To overcome the above problem with BPA, nanoparticle-based drugs (nanodrugs) that can selectively deliver boron atoms into a cancer cell and maintain the boron atoms have been studied, and various boron-containing nanoparticles have been reported to date (Non-Patent Literature 1).

CITATION LIST

Patent Document

Patent Document 1: JP 2009-51766 A

Non-Patent Literature

Non-Patent Literature 1: T. Nomoto. et. al., Sci. Adv. 2020, 6, eaaz1722

SUMMARY OF INVENTION

Technical Problem

Some of these drugs show promising results but are difficult to mass produce and raise concerns over quality due to lack of reproducibility. In addition, improved stability under physiological conditions is also desirable.

Thus, an object of the present disclosure is to provide a surface-modified nanoparticle that can be easily produced and can selectively deliver boron atoms into a cancer cell and maintain the boron atoms, and a method for producing the surface-modified nanoparticle.

Solution to Problem

Diligent research by the inventors of the present disclosure to achieve the above object has found that a surface-modified nanoparticle including:

a nanocarbon material; and a surface-modifying group of the nanocarbon material, in which the surface-modified nanoparticle has a group containing a hydrophilic polymer chain and a group containing a boron atom as the surface-modifying groups can be easily produced and have excellent stability under physiological conditions. The invention according to the present disclosure was completed based on these findings.

That is, the present disclosure relates to a surface-modified nanoparticle including:

a nanocarbon material; and a surface-modifying group of the nanocarbon material, in which the surface-modified nanoparticle has a group containing a boron atom as the surface-modifying group.

The nanocarbon material is preferably a nanodiamond particle.

The surface-modified nanoparticle preferably has a group containing a hydrophilic group and a boron atom as the surface-modifying groups.

The hydrophilic group is preferably a group containing a hydrophilic polymer chain.

The surface-modified nanoparticle preferably has a group containing a boron atom and a hydrophilic polymer chain as the surface-modifying group.

The hydrophilic polymer chain is preferably a polyglycerol chain.

The polyglycerol chain is preferably a polyglycerol chain in which one, some, or all of hydroxyl groups is/are replaced by an amino group(s).

At least one or some of the amino group(s) is/are preferably protected by a compound having an acidic functional group.

The boron atom is preferably bonded to the hydrophilic polymer chain via an aromatic ring.

The boron atom is preferably directly bonded to the aromatic ring.

The aromatic ring is preferably bonded to the hydrophilic polymer chain via an alkyleneoxy group or an alkyleneamino group bonded to a carbon atom constituting the aromatic ring.

The boron atom and the alkyleneoxy group or alkyleneamino group are each preferably bonded to carbon atoms adjacent to each other among carbon atoms constituting the aromatic ring.

The aromatic ring is bonded to the hydrophilic polymer chain via an alkyleneamino group bonded to a carbon atom constituting the aromatic ring, and the amino group in the alkyleneamino group is preferably a tertiary amino group.

The aromatic ring is preferably a benzene ring or a pyridine ring.

The aromatic ring preferably contains an electron-withdrawing group as a substituent.

The electron-withdrawing group is preferably a fluorine atom.

The boron atom is preferably contained as a boronic acid.

The boron atom is preferably enriched in $^{10}$B.

For the surface-modified nanoparticle, when 0.5 parts by mass of the surface-modified nanoparticle is blended with 99.5 parts by mass of a PBS (pH 7.4)/FBS (45/55 (v/v)) solution and the solution is stored at 25° C., preferably substantially no aggregate forms within 10 minutes as determined by visual inspection.

In addition, the present disclosure also describes a composition for use in boron neutron capture therapy, the composition containing the surface-modified nanoparticle.

Advantageous Effects of Invention

The surface-modified nanoparticle of the present disclosure can be easily produced, selectively deliver boron atoms into cancer cells, and also maintain the concentration of boron atoms in the cancer cells. In addition, the surface-modified nanoparticle of the present disclosure further having a hydrophilic group as the surface-modifying group achieves an effect of improving stability under physiological conditions. Thus, the surface-modified nanoparticle of the present disclosure can accumulate a sufficient amount of boron atoms in cancer tissues and/or cancer cells, and thus can effectively kill cancer tissues and/or cancer cells by boron neutron capture therapy (BNCT).

DESCRIPTION OF EMBODIMENTS

Surface-Modified Nanoparticle

Figure 1:
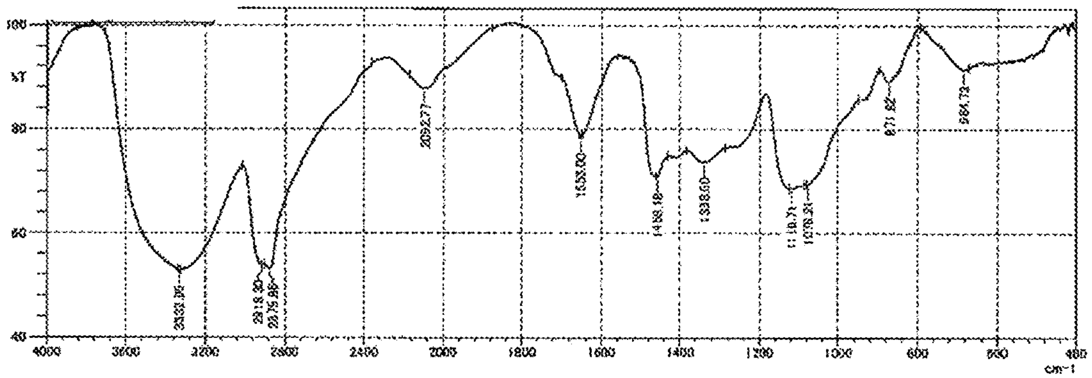
FIG. 1 is a graph showing a FT-IR spectrum of DND-PG.

A surface-modified nanoparticle of the present disclosure includes a nanocarbon material and a surface-modifying group that modifies the surface of the nanocarbon material. The surface-modified nanoparticle has at least a group containing a boron atom as the surface-modifying group. In addition, from the viewpoint of stability under physiological conditions, the surface-modified nanoparticle preferably further has a hydrophilic group as the surface-modifying group. That is, the surface-modified nanoparticle preferably has a hydrophilic group and a group containing a boron atom as surface-modifying groups.

The nanocarbon material is not particularly limited, and examples include a nanodiamond, a nanographene, a graphene nanoribbon, a fullerene, graphene oxide, a nanographite, a carbon nanotube, a carbon nanofilament, an onion-like carbon, a diamond-like carbon, an amorphous carbon, a carbon black, a carbon nanohorn, and a carbon nanocoil. Of these, a nanodiamond is preferred since boron atoms can be sufficiently accumulated in cancer tissues and/or cancer cells. In addition, the nanodiamond is preferably a particulate nanodiamond (nanodiamond particle). Hereinafter, "nanodiamond" may be referred to as "ND".

The nanodiamond (particle) is not particularly limited, and examples that can be used include a detonation ND, an ND obtained by a high temperature-high pressure method, and an ND obtained by a chemical vapor deposition method (an ND obtained by pulverizing a diamond thin film prepared by a CVD method). Of these, a detonation ND is preferred due to having even better dispersibility in a dispersion medium and having a single-digit nanometer particle size with regard to the primary particles. A defect with fluorescent properties or magnetic properties, such as a nitrogen-vacancy center (a NV center) or a silicon-vacancy center (a SiV center), may be present in the diamond crystal structure of the nanodiamond.

The hydrophilic group is not particularly limited, and examples include a hydroxyl group, a carboxyl group, a sulfo group, an amino group, and a group containing a hydrophilic polymer chain. Of those, from the viewpoint of further improving stability under physiological conditions, a group containing a hydrophilic polymer chain is preferred. That is, the surface-modified nanoparticle preferably has a group containing a hydrophilic polymer chain and a group containing a boron atom as the surface-modifying groups.

In the surface-modified nanoparticle having a group containing a hydrophilic polymer chain and a group containing a boron atom as the surface-modifying groups, these groups may be the same surface-modifying group or may be different surface-modifying groups. That is, the hydrophilic polymer chain and the boron atom may be present in one surface-modifying group or may be present in different surface-modifying groups. An example of an aspect in which the hydrophilic polymer chain and the boron atom are present in one surface-modifying group is a group containing a boron atom and a hydrophilic polymer chain. The surface-modified nanoparticle of the present disclosure may have only one type of the surface-modifying group described above or may have two or more types of the surface-modifying groups described above.

The ND particle constituting the surface-modified nanoparticle preferably contains primary particles of nanodiamond. Additionally, the ND particle may contain secondary particles in which a plurality of the primary particles are aggregated (agglutinated). Furthermore, the surface-modified nanoparticle may have one type or two or more types of functional groups other than the hydrophilic group and the group containing boron on the surface of the surface-modified nanoparticle (surface of the ND particle). Examples of such a functional group include an amino group, a hydroxyl group, and a carboxyl group.

An example of the hydrophilic polymer chain is a polymer chain containing a structural unit derived from a monomer having a hydrophilic group, such as a polyether chain (such as poly(ethylene oxide), poly(propylene oxide), and copolymers of these), and polyglycerol chains (such as $C_3H_6O(CH_2CH(OH)CH_2O)n\text{-}H$). Of these, the hydrophilic polymer chain is preferably a polyglycerol chain from the viewpoint of stability under physiological conditions. That is, the hydrophilic polymer chain preferably includes a polyglycerol chain.

The polyglycerol chain is preferably the polyglycerol chain represented by Formula (1) below.

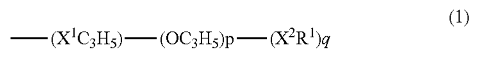

(1)

where in Formula (1), p represents an integer of 1 or more and q represents an integer satisfying q=p+2; $X^1$ represents a divalent group, with a bond extending leftward from $X^1$ in $[X^1C_3H_5]$ being bonded to the nanocarbon material; $[X^2R^1]$ represents a terminal of the polyglycerol chain; $X^2$ represents a single bond or a divalent group; and $R^1$ represents a hydrogen atom or a monovalent organic group.

$[X^1C_3H_5]$ in Formula (1) above is represented by $[—X^1—CH_2—C(-)H—CH_2—]$. $X^1$ in $[X^1C_3H_5]$ above is bonded to the nanocarbon material, and two C atoms each bind to O in $[OC_3H_5]$ or $X^2$ in $[X^2R^1]$. $X^1$ in $[X^1C_3H_5]$ above represents a divalent group. One or more $R^1$s are monovalent organic groups, and the one or more monovalent organic groups in $R^1$s preferably contain a boron atom.

Examples of the divalent group in $X^1$ include an amino group ($—NR^a—$), an amide group ($—NR^a—C(═O)—$), an ether bond (—O—), an ester bond (—O—C(═O)—), a phosphinic acid group (—PH(═O)O—), a phosphonic acid group (—P(—OH)(═O)O—), a phosphate ester (—O—P(═O)(OH)—O—), a sulfide bond (—S—), a carbonyl group (—C(═O)—), a urethane bond ($—R^aN—C(═O)—O—$), an imide bond ($—C(═O)—NR^a—C(═O)—$), a thiocarbonyl group (—C(═S)—), a siloxane bond (—Si—O—), a sulfate ester group ($—O—S(═O)_2—O—$), a sulfonyl group ($—S(═O)_2—O—$), a sulfonic group ($—S(═O)_2—$), a sulfoxide (—S(═O)—), and groups in which two or more of these are bonded. In an asymmetric divalent group, the direction of the divalent group with respect to the nanocarbon material side and the R side is not limited. In addition, $R^a$ above represents a hydrogen atom or a monovalent organic group. Of those above, the divalent group is preferably $—NR^a—$, —O—, —C(═O)O—, $—NR^a—C(═O)—$, —PH(═O)O—, or —S—, more preferably $—NR^a—$, —O—, $—NR^a—C(═O)—$, or —C(═O)O—.

Examples of the monovalent organic group in $R^1$ include a substituted or unsubstituted hydrocarbon group (a monovalent hydrocarbon group, particularly a monovalent aliphatic or aromatic hydrocarbon group), a substituted or unsubstituted heterocyclic group (monovalent heterocyclic group), and a group in which two or more of the monovalent hydrocarbon groups and/or the monovalent heterocyclic groups are bonded. The bonded groups may be directly bonded or may be bonded via a linking group. Examples of the linking group include an amino group, an ether bond, an ester bond, a phosphinic acid group, a sulfide bond, a carbonyl group, an organic group-substituted amide group, an organic group-substituted urethane bond, an organic group-substituted imide bond, a thiocarbonyl group, a siloxane bond, and a group in which two or more of these are bonded.

$[OC_3H_5]$ with p in Formula (1) above is a structure derived from a glycerol represented by $[—O—CH_2—C(-)H—CH_2—]$ and forms a polyglycerol chain together with $[X^1C_3H_5]$. p represents a repeating unit of $[OC_3H_5]$ and is an integer of 1 or more, preferably from 3 to 2000, more preferably from 5 to 500, and even more preferably from 10 to 200. p may be identical or different in the group containing the plurality of polyglycerol chains.

In Formula (1) above, $[X^2R^1]$ represents a terminal of the polyglycerol chain and binds to C in $[X^1C_3H_5]$ or C in $[OC_3H_5]$. $R^1$ represents a hydrogen atom or a monovalent organic group.

$X^2$ in $[X^2R^1]$ above represents a single bond or a divalent group. Examples of the divalent group include the divalent groups exemplified and described as $X^1$ in $[X^1C_3H_5]$ described above. In addition, $R^a$ and $R^1$ in $X^2$ may bond to each other to form a ring. Among these, $X^2$ is preferably $—NR^a—$, $—NR^aC(═O)—$, —O—, —C(═O)O—, —O—C(═O)—, —PH(═O)O—, —O—P(═O)(OH)—O—, —S—, $—O—S(═O)_2—O—$, or $—O—S(═O)_2—$, and more preferably $—NR^a—$ or —O—. $X^1$ in $[X^1C_3H_5]$ above and $X^2$ in $[X^2R^1]$ above may be identical or different. The plurality of $[X^2R^1]$s above may be identical or different. In addition, $X^2$ in $[X^2R^1]$ above may be identical or different in the group containing a plurality of polyglycerol chains. q represents an integer of 3 or more, and the value of q depends on the value of p and satisfies q=p+2. q may be identical or different in the group containing a plurality of polyglycerol chains.

When $R^1$ above is a monovalent organic group, a plurality of $R^1$s in Formula (1) above may be identical or different. Examples of the monovalent organic group include those exemplified and described as the monovalent organic group in $R^a$ above. Among those, examples of the monovalent organic group include a substituted or unsubstituted hydrocarbon group (monovalent hydrocarbon group), a substituted or unsubstituted heterocyclic group (monovalent heterocyclic group), and a group in which two or more of these are bonded. The monovalent organic group may have an ionic form.

The bonded groups may be directly bonded or may be bonded via a linking group. The hydrocarbon group in the substituted or unsubstituted hydrocarbon group is preferably an alkyl group, more preferably an alkyl group containing from 1 to 18 carbon atoms, even more preferably an alkyl group containing from 1 to 6 carbon atoms, and particularly preferably an ethyl group, a propyl group, a butyl group, or a hexyl group.

Specific examples of $[X^2R^1]$ include OH, $NH_2$, $CH_3$, an alkoxy group, an acyl group, a mono- or di-alkylamino group, a mono- or di-alkenylamino group, an alkylamide group, an alkenylamide group, a quatemary ammonium-substituted alkoxy group, a chlorine-substituted alkoxy group, a polyalkylene oxide group, a cyclic imido group, a carboxyl-substituted alkylamino group, a carboxyl-substituted alkyloxy group, and a group containing a boron atom. Two or more [$X^2R^1$] above may form a ring via $R^1$. Of these, from the viewpoint of even better water dispersibility of the surface-modified nanoparticle and from the viewpoint of easy introduction of a boron atom, [$X^2R^1$] is preferably a cyclic imido group, a carboxyl-substituted alkylamino group, or a group containing a boron atom.

The number-average degree of polymerization of glycerol in the polyglycerol chain is preferably from 3 to 2000, more preferably from 5 to 500, and even more preferably from 10 to 200. When the number-average degree of polymerization is high, mutual repulsive forces sufficiently act between the nanocarbon materials, such as nanodiamond particles, and the dispersibility of the nanocarbon material can be even further improved. When the number-average degree of polymerization is 5000 or less, the polyglycerol chains are less likely to become tangled between the nanocarbon materials, such as nanodiamond particles, and this can further improve the dispersibility of the nanocarbon material in water. The number-average degree of polymerization is defined by the number of glycidol units constituting the polyglycerol chain in a group bonded to a surface functional group 1 of the nanocarbon material, such as nanodiamond, as the raw material. The number of surface functional groups can be determined by elemental analysis value measurement or acid value measurement of the raw material, or by a combination of these methods.

The polyglycerol chain is preferably a polyglycerol chain in which one, some, or all of hydroxyl groups in the polyglycerol chain is/are replaced by an amino group(s) (hereinafter referred to as "nitrogen-substituted polyglycerol chain"). Examples of the nitrogen-substituted polyglycerol chain include a polyglycerol chain represented by Formula (1) above in which at least one or some of $X^2$s is/are an amino group(s).

At least one or some of the amino groups in the nitrogen-substituted polyglycerol chain may be protected by a compound containing an acidic functional group for the purpose of improving the dispersibility of the surface-modified nanoparticle in blood (preventing aggregation in blood). An example of such a polyglycerol chain is a polyglycerol chain represented by Formula (1) above in which at least one or some of $X^2$ are amino groups ($-NR^a-$) and at least one or some of $R^a$ are protecting groups. Examples of the acidic functional group include a carboxyl group and a sulfonyl group. Specific examples of the compound containing an acidic functional group include dicarboxylic acids, such as oxalic acid, malonic acid, succinic acid, glutaric acid, and adipic acid; acid anhydrides, such as oxalic anhydride, succinic anhydride, maleic anhydride, phthalic anhydride, and benzoic anhydride; and compounds containing a sulfonyl group, such as sulfuric acid. Of these, an acid anhydride is preferred from the viewpoint of forming an amide bond and having a carboxyl group at the terminal, and even further improving the dispersibility of the surface-modified nanoparticle in blood. Examples of other protective groups include alkyl groups, such as a methyl group, an ethyl group, and a propyl group; and cycloalkyl groups, such as a benzyl group and a phenyl group.

The surface-modified nanoparticle preferably has a group containing a boron atom and a hydrophilic polymer chain as the surface-modifying group. In this case, the boron atom is preferably bonded to the nanocarbon material via the hydrophilic polymer chain. The boron atom is more preferably bonded to the hydrophilic polymer chain via an aromatic ring. The boron atom may be bonded to the aromatic ring directly or via another linking group, and is preferably bonded to the aromatic ring directly, particularly preferably bonded to a carbon atom constituting the aromatic ring. The surface-modified nanoparticle may have only one type of aromatic ring described above or may have two or more types of aromatic rings described above.

Examples of the aromatic ring include an aromatic hydrocarbon ring and an aromatic heterocycle. Examples of the hydrocarbon ring include $C_{6-14}$ hydrocarbon rings (particularly $C_{6-10}$ hydrocarbon rings), such as a benzene ring and a naphthalene ring. Examples of the aromatic heterocycle include rings having a carbon atom and at least one type of heteroatom (e.g., an oxygen atom, a sulfur atom, or a nitrogen atom) in atoms constituting the ring, and fused rings of these.

The aromatic ring is preferably a four- to ten-membered ring, more preferably a six-membered ring. Examples of the 6-membered aromatic ring include a benzene ring and a pyridine ring.

The aromatic ring may or may not have a substituent. Examples of the substituent include a halogen atom, such as a fluorine atom, a chlorine atom, a bromine atom, and an iodine atom; a hydroxyl group; a mercapto group; a carboxy group; an amino group; and an oxo group. Of these, the aromatic ring preferably has an electron-withdrawing group, such as a fluorine atom, as the substituent. The aromatic ring has the electron-withdrawing group preferably at a meta position with respect to the bonding position of the boron atom in the aromatic ring. The substituent corresponds to $R^3$ in Formula (2) to be described later.

The aromatic ring is preferably bonded to the hydrophilic polymer chain via an alkyleneoxy group or alkyleneamino group bonded to a carbon atom constituting the aromatic ring. More specifically, the aromatic ring is preferably bonded to the hydrophilic polymer chain via an alkyleneoxy group bonded to a carbon atom constituting the aromatic ring or an alkyleneamino group bonded to a carbon atom constituting the aromatic ring. In this case, the dispersibility of the ND is improved, thus tending to provide excellent stability under physiological conditions. In addition, the surface-modified nanoparticle can be easily prepared by utilizing an oxygen atom in the polyglycerol chain as the oxygen atom in the alkyleneoxy group and a nitrogen atom in the nitrogen-substituted polyglycerol chain as the nitrogen atom in the alkyleneamino group.

Examples of the alkylene group in the alkyleneoxy group and the alkyleneamino group include a methylene group, an ethylene group, a propylene group, and a trimethylene group. From the viewpoint of improving the dispersibility of the surface-modified nanoparticle, the alkylene group is preferably an alkylene group containing from 1 to 6 carbon atoms, more preferably an alkylene group containing from 1 to 3 carbon atoms, and even more preferably a methylene group.

The amino group in the alkyleneamino group may be a secondary amino group or a tertiary amino group. When the amino group is a tertiary amino group, the amino group contains the alkylene group, the hydrophilic polymer chain, and a monovalent organic group on the nitrogen atom in the amino group. An example of the monovalent organic group is a hydrocarbon group. The monovalent organic group is preferably an alkyl group, more preferably an alkyl group containing from 1 to 6 carbon atoms, even more preferably an alkyl group containing from 1 to 3 carbon atoms, and particularly preferably a methyl group. The monovalent organic group corresponds to $R^5$ in Formula (2) to be described later.

The boron atom and the alkyleneoxy group or alkyleneamino group are each preferably bonded to carbon atoms adjacent to each other among the carbon atoms constituting the aromatic ring. That is, the aromatic ring contains the alkyleneoxy group or alkyleneamino group preferably at an ortho position with respect to the bonding position of the boron atom in the aromatic ring. In addition, in this case, the aromatic ring has the electron-withdrawing group preferably at a meta position with respect to the bonding position of the boron atom on the side having the alkyleneoxy group or alkyleneamino group.

An aspect in which the boron atom is directly bonded to a carbon atom constituting the aromatic ring and the aromatic ring is bonded to the hydrophilic polymer chain via an alkyleneoxy group or alkyleneamino group bonded to a carbon atom constituting the aromatic ring will be described using a group represented by Formula (2) below.

[Chem. 1]

(2)

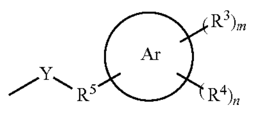

In Formula (2), Ar represents an aromatic ring and $R^3$ represents a substituent that the aromatic ring may have. The substituent is preferably, for example, an electron-withdrawing group. m is an integer of 0 or more. $R^4$ is a group containing a boron atom, in which the boron atom is directly bonded to a carbon atom constituting the aromatic ring. n is an integer of 1 or more. $R^5$ represents an alkylene group and is a group identical to the alkylene group in the alkyleneoxy group and the alkyleneamino group. Y is an oxygen atom, NH, or $NR^6$. $R^6$ is a monovalent organic group. The bond extending leftward from Y is bonded to a hydrophilic polymer chain (preferably a polyglycerol chain).

The group represented by Formula (2) above is particularly preferably a group represented by Formula (3) below.

[Chem. 2]

(3)

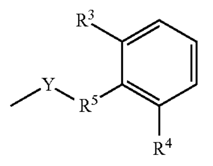

In Formula (3), $R^3$, $R^4$, $R^5$, and Y are identical to those described in Formula (2). Formula (3) shows an aspect in which the boron atom and the alkyleneoxy group or alkyleneamino group of $R^4$ are each bonded to carbon atoms adjacent to each other the among carbon atoms constituting the aromatic ring.

In the group containing a boron atom, the boron atom may be bonded to a hydrogen atom, a hydroxyl group, an amino group, a sulfo group, a monovalent organic group, or another substituent. Examples of the group containing a boron atom include compounds represented by Formula (4) below.

(4)

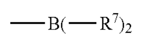

In Formula (4), $R^7$s are identical to or different from each other and represent a hydrogen atom, a hydroxyl group, an amino group, a sulfo group, or a monovalent organic group. In addition, two $R^7$s may be bonded to each other to form a ring (hydrocarbon-containing ring). When two $R^7$s are bonded to each other to form a ring, the ring may be formed via an oxygen atom. Furthermore, carbons constituting the ring may form a double bond with an adjacent carbon atom. The number of carbons constituting the ring is not particularly limited and is, for example, preferably from 4 to 12, more preferably from 4 to 10, and even more preferably from 4 to 6.

An example of the monovalent organic group is a hydrocarbon group. The monovalent organic group is preferably an alkyl group, more preferably an alkyl group containing from 1 to 6 carbon atoms, even more preferably an alkyl group containing from 1 to 3 carbon atoms, and particularly preferably a methyl group.

Specific examples of the group represented by Formula (3) above include those in which $R^7$ is a hydrogen atom or a hydroxyl group, such as boronic acid ($-B(OH)_2$) and borane ($-BH_2$), and the group is particularly preferably boronic acid, in which $R^7$ is a hydroxyl group. That is, in the surface-modified nanoparticle of the present disclosure, the boron atom is preferably contained as boronic acid.

The content of the boron atom in the surface-modified nanoparticle of the present disclosure is not particularly limited and is, for example, preferably 0.1 mass % or more, more preferably 0.5 mass % or more, even more preferably 1.0 mass % or more, and particularly preferably 1.5 mass % or more. When the content of the boron atom is in the above range, the surface-modified nanoparticle tends to have excellent stability under physiological conditions and be able to selectively deliver boron atoms into cancer cells and retain the boron atoms. The content of the boron atom is, for example, 10.0 mass % or less.

The boron atom may be any isotope, such as $^{10}B$ and $^{11}B$, and is not particularly limited. Of those, the boron is preferably enriched in $^{10}B$.

The mass ratio of the ND to the surface-modifying group [ND/surface-modifying group of present disclosure] in the surface-modified nanoparticle of the present disclosure is not particularly limited and is preferably from 0.2 to 1.5 and more preferably from 0.2 to 1.0. When the mass ratio is 0.2 or higher, the surface-modified nanoparticle is less likely to lose properties as a nanodiamond material. When the mass ratio is 1.5 or less (particularly 1.0 or less), the surface is modified to a sufficient degree with the surface-modifying group, and the surface-modified nanoparticle has even better dispersibility under physiological conditions. The mass ratio is determined based on a weight loss rate measured by a thermogravimetric analysis of a sample before introducing a boron substituent as a ratio of weight of the remaining ND to a sum of the weight loss regarded as mass of the polyglycerol chain-containing surface-modifying group before introducing the boron substituent and weight of the boron substituent to be introduced here.

The mean volume particle size (MV) of the surface-modified nanoparticle of the present disclosure is, for example, 200 nm or less, preferably 100 nm or less, and more preferably 60 nm or less. The lower limit of the mean particle size (MV) of the surface-modified nanoparticle is, for example, 5 nm. The mean particle size of the surface-modified nanoparticle can be measured by a dynamic light scattering method.

The surface-modified nanoparticle of the present disclosure can be used in boron neutron capture therapy of tumor diseases.

Examples of the "tumor diseases" in the present specification include malignant melanoma, renal cancer, prostate cancer, breast cancer, lung cancer, pancreatic cancer, bowel cancer, hepatocellular carcinoma, biliary tract cancer, gastric cancer, ovarian cancer, esophageal cancer, urothelial carcinoma, colon cancer, bone cancer, skin cancer (e.g., malignant skin cancer), head and neck cancer, rectal cancer, cancer of the anal region, testicular cancer, uterine cancer, fallopian tube cancer, endometrial cancer, cervical cancer, vaginal cancer, small intestinal cancer, endocrine system cancer, thyroid cancer, parathyroid cancer, adrenal cancer, soft tissue sarcoma, urethral cancer, penile cancer, pediatric solid cancer, bladder cancer, malignant pleural mesothelioma, brain tumors (e.g., malignant brain tumors), and central nervous system tumors.

Boron neutron capture therapy using the surface-modified nanoparticle is performed by, for example, administering a drug containing the surface-modified nanoparticle to a mammal (e.g., a human) suffering from a tumor disease by any suitable route of administration that accumulates the compound at the target site. Preferably, the surface-modified nanoparticle is selectively accumulated in a tumor. A formulation containing the compound may be administered all at once or sequentially. Administration of the formulation may be repeated as necessary.

After the surface-modified nanoparticle reaches the tumor, the site is irradiated with an effective amount of a low-energy neutron beam, such as a thermal neutron beam or an epithermal neutron beam. The site may be irradiated through the skin, or the site may be fully or partially exposed before irradiation and then irradiated. The administration of the surface-modified nanoparticle and the subsequent irradiation with the thermal neutron beam or epithermal neutron beam may be repeated as necessary.

The route of administration of the surface-modified nanoparticle is preferably intravenous administration, intraarterial administration, intramuscular administration, subcutaneous administration, intradermal administration, intraspinal administration, or intraperitoneal administration.

The surface-modified nanoparticle can be administered to a mammal suffering from a tumor disease within 72 hours (preferably from 5 minutes to 48 hours and more preferably from 30 minutes to 30 hours) before irradiation with the thermal neutron beam or epithermal neutron beam. Alternatively, the surface-modified nanoparticle may be administered during irradiation with the thermal neutron beam or epithermal neutron beam. Atypical dose of the surface-modified nanoparticle is preferably in a range from 0.01 mg to 5000 mg/kg of body weight per irradiation with the thermal neutron beam or epithermal neutron beam. The boron-10 ($^{10}B$) dosage is preferably in a range from 0.005 mg to 1000 mg/kg of body weight per irradiation with the thermal neutron beam or epithermal neutron beam. The irradiation time per irradiation with the thermal neutron beam or epithermal neutron beam is preferably from 1 minute to 5 hours and more preferably from 10 minutes to 2 hours. The irradiation amount of the thermal neutron beam or epithermal neutron beam is not particularly limited and is an irradiation amount commonly used in neutron capture therapy.

The boron neutron capture therapy using the surface-modified nanoparticle may be applied as a single treatment or may be applied in combination with surgery or chemotherapy in the related art. If desired, after removing a tumor to the best possible surgical extent, the remaining tumor can be destroyed by the boron neutron capture therapy using the surface-modified nanoparticle.

A composition containing the surface-modified nanoparticle can be used in the boron neutron capture therapy. In the composition, the surface-modified nanoparticle may be used as it is as an active ingredient, or the composition may be formulated by adding a pharmaceutically acceptable excipient or the like. In addition, as described above, the composition may contain another boron compound, such as BPA or BSH.

Examples of the excipient include, but are not limited to, purified water; saline; a phosphate buffer; dextrose; pharmaceutically acceptable organic solvents such as glycerol and ethanol; animal and vegetable oils; glucose; mannose; fructose; galactose; sorbitol; mannitol; crystalline cellulose; hydroxypropyl cellulose; starch; corn starch; silicic anhydride; magnesium aluminum silicate; collagen; poly(vinyl alcohol); polyvinylpyrrolidone, carboxyvinyl polymers; sodium carboxymethylcellulose; sodium polyacrylate; sodium alginate; water-soluble dextran; sodium carboxymethylstarch; pectin; methylcellulose; ethylcellulose; xanthan gum; gum arabic; tragacanth; casein; agar; polyethylene glycol; diglycerol; glycerol; propylene glycol; Vaseline; paraffin; octyldodecyl myristate; isopropyl myristate; higher alcohols; stearyl alcohol; stearic acid; and human serum albumin.

The surface-modified nanoparticle may be formulated with a pharmaceutically acceptable solvent; and/or a pharmaceutically acceptable carrier, such as a filler, a binder, a stabilizer, and/or a dispersant, into a parenteral dosage form, such as a solution for injection, a suspension, an emulsion, a cream, an ointment, an inhalant, or a suppository. The surface-modified nanoparticle is preferably formulated into a solution for injection.

The solution for injection can be produced as a solution of the surface-modified nanoparticle in a pharmaceutically acceptable solvent. Those solutions may also contain a stabilizing component and/or a buffering component. In addition, the solution for injection may be a dry formulation to be used by adding a suitable solvent before use.

Method for Producing Surface-Modified Nanoparticle

The surface-modified nanoparticle of the present disclosure can be produced by reacting a nanocarbon material (e.g., an ND particle), a hydrophilic polymer, and a boron-containing compound. The hydrophilic polymer and the boron-containing compound may be reacted with the nanocarbon material simultaneously or separately. For example, after reacting the nanocarbon material with the hydrophilic polymer, the resulting reaction product may be reacted with the boron-containing compound, or after reacting the nanocarbon material with the boron-containing compound, the resulting reaction product may be reacted with the hydrophilic polymer. In addition, the nanocarbon material, the hydrophilic polymer, and the boron-containing compound may be reacted at once. Of these, reacting the nanocarbon material with the hydrophilic polymer and then reacting the resulting reaction product with the boron-containing compound is preferred because the intended surface-modified nanoparticle can be easily obtained.

The boron-containing compound is not particularly limited and is appropriately selected according to, for example, an aspect in which a boron atom is introduced. Examples include compounds corresponding to groups represented by Formula (4) above, specifically, compounds represented by Formula (5) below.

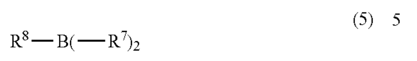

(5)

In Formula (5), $R^7$ is identical to that in Formula (4). $R^8$ represents a hydrogen atom or a monovalent organic group.

Examples of the monovalent organic group include those described above. The monovalent organic group preferably has an aromatic ring. The boron-containing compound is preferably 2-formylphenylboronic acid (o-boromobenzaldehyde) from the viewpoints of ease of production and stability under physiological conditions.

The hydrophilic polymer is any polymer containing a structural unit derived from a monomer having a hydrophilic group and is not particularly limited, and examples include polyethers (such as poly(ethylene oxide), poly(propylene oxide), and copolymers of these) and polyglycerols (such as $C_3H_6O(CH_2CH(OH)CH_2O)n\text{-}H$). The polyglycerol may be a polyglycerol in which one, some, or all hydroxyl groups is/are replaced by an amino group(s).

The surface-modified nanoparticle may have only one type each of the hydrophilic polymer and the boron-containing compound or may have two or more types each of the hydrophilic polymer and the boron-containing compound.

The method of reacting the nanocarbon material with the hydrophilic polymer is not particularly limited and can be a known and commonly used method. A specific example of using a polyglycerol as the hydrophilic polymer will be described below.

The method for modifying the surface of the nanocarbon material with a polyglycerol is not particularly limited. The surface-modified nanoparticle can be obtained by, for example, ring-opening polymerization of glycidol on the nanocarbon material. Taking an example of using an ND particle as the nanocarbon material, since the ND particle naturally has a carboxyl group, a hydroxyl group, and/or the like on the particle surface in the production process, the ND particle surface can be modified with a polyglycerol chain by reacting these functional groups with glycidol.

The ND particle can be reacted with glycidol (ring-opening polymerization) by, for example, adding glycidol and a solvent to the ND particle in an inert gas atmosphere and heating to 50 to 150° C. For the solvent, for example, an aliphatic alcohol solvent containing from 2 to 4 carbon atoms can be used. For the aliphatic alcohol solvent containing from 2 to 4 carbon atoms, the solvent described in WO 2021/039521 A1 can be used.

A catalyst can be used in the reaction. An acidic catalyst or a basic catalyst can be used as the catalyst. Examples of the acidic catalyst include boron trifluoride etherate, acetic acid, and phosphoric acid. Examples of the basic catalyst include triethylamine, pyridine, dimethylaminopyridine, and triphenylphosphine.

For the conditions of the ring-opening polymerization of glycidol, the following can be used as resources: S. R. Sandler et al., J. Polym. Sci., Polym. Chem. Ed., Vol. 4, 1253 (1966); E. J. Vanderberg, J. Polym. Sci., Polym. Chem. Ed., vol. 23, 915 (1985); and G. R. Newcome et al., Dendritic Macromolecules: Concepts, Syntheses, Perspectives, VCH, Weinheim (1996).

In addition, the ND particle surface-modified with a polyglycerol chain can be obtained by ring-opening polymerization of glycidol on an ND particle in which a functional group containing active hydrogen is introduced to its surface. The functional group containing active hydrogen is not particularly limited, and examples include an amino group, a hydroxyl group, a carboxyl group, a mercapto group (a thiol group), and a phosphinic acid group. For the method for introducing the functional group containing the active hydrogen into the ND particle, the following can be used as resources: JP 2012-82103 A and JP 2010-248023 A. The ring-opening polymerization of glycidol on the ND particle in which a functional group containing active hydrogen is introduced to the surface can be carried out in the same manner as the ring-opening polymerization of glycidol on an ND particle described above.

The method of reacting the nanocarbon material with the boron-containing compound is not particularly limited and can be a known and commonly used method. Taking an example of using an ND particle as the nanocarbon material, a group containing a boron atom can be introduced by reacting a functional group, such as a carboxyl group and/or a hydroxyl group, present on the surface of the ND particle, with a boron-containing compound in the same manner as in the case of reacting a polyglycerol serving as the hydrophilic polymer with the ND particle.

When the surface-modified nanoparticle of the present disclosure is produced by a method in which an ND particle is reacted with a hydrophilic polymer and then the resulting reaction product is reacted with a boron-containing compound, the boron-containing compound may be reacted with a hydrophilic polymer chain in the reaction product or may be reacted with a functional group present on the surface of the ND particle. In the case of the former reaction, the surface-modified nanoparticle of the present disclosure has a surface-modifying group to which a boron atom is bonded via the hydrophilic polymer chain. In the case of the latter reaction, the surface-modified nanoparticle of the present disclosure has a group containing a boron atom on the ND particle surface as a surface-modifying group.

For the method in which the surface-modified nanoparticle is obtained by reacting an ND particle with a hydrophilic polymer and then reacting the resulting reaction product with a boron-containing compound, an example of using a polyglycerol as the hydrophilic polymer will be described below.

The method for modifying the surface of an ND particle with a polyglycerol is as described above. In the reaction between the resulting ND particle and the boron-containing compound, the terminal oxygen atom of the polyglycerol chain may be replaced by a nitrogen atom for the purpose of improving the reactivity. In addition, to avoid aggregation of the surface-modified nanoparticle of the present disclosure, the nitrogen atom may be protected with a protecting group after the reaction with the boron-containing compound. Examples of the protective group include groups derived from the compound having an acidic functional group described above, and specific examples include a methyl group, a succinyl group, a sulfate group, and a phosphate group.

The ND particle before surface modification is not particularly limited in terms of its production method, and examples that can be used include a detonation ND (i.e., an ND produced by a detonation method, which may be referred to as a "DND"), a high-temperature-high pressure ND (i.e., an ND produced by a high temperature-high pressure method), and an ND obtained by a chemical vapor deposition method (an ND obtained by pulverizing a diamond thin film prepared by a CVD method). Of these, the detonation ND is preferred in terms of even better dispersibility in a dispersion medium, that is, in that the primary particles have a particle size of a single-digit nanometer.

The mean particle size of the ND particle before surface modification is not particularly limited and is, for example, 100 nm or less, preferably 50 nm or less, more preferably 30 nm or less, and particularly preferably 10 nm or less. The lower limit of the mean particle size of the ND particle is, for example, 0.1 nm. The mean particle size of the surface-modified nanoparticle can be measured by a dynamic light scattering method.

Each aspect disclosed in the present specification can be combined with any other feature disclosed herein. Note that each of the configurations, combinations thereof, or the like in each of the embodiments are examples, and additions, omissions, replacements, and other changes to the configurations may be made as appropriate without departing from the spirit of the present disclosure. In addition, each aspect of the invention according to the present disclosure is not limited by the embodiments or the following examples but is limited only by the claims.

EXAMPLES

Hereinafter, the present disclosure will be described in more detail based on examples, but the present disclosure is not limited by the examples.

A surface-modified ND was produced by the following processes.

Preparation of Detonation ND "DND"

A molded explosive including an electric detonator was placed inside a pressure-resistant vessel for detonation, and the vessel was sealed. The vessel was made of iron and had a capacity of 15 $m^3$. For the explosive, 0.50 kg of a mixture of TNT and RDX was used. The mass ratio of the TNT and RDX (TNT/RDX) in the explosive was 50/50. The electric detonator was then triggered to detonate the explosive in the vessel (production of a DND, an ND by a detonation method). Then, the vessel was allowed to stand at room temperature for 24 hours to lower the temperatures of the vessel and its interior. After this cooling, a DND crude product (containing soot and an aggregate of DND particles) was collected by scraping the DND crude product deposited on the inner wall of the vessel with a spatula.

The DND crude product obtained by performing the process described above multiple times was subjected to oxidation treatment. Specifically, 6 L of a 10 mass % hydrochloric acid was added to 200 g of the DND crude product to prepare a slurry, and the slurry was subjected to a heating treatment for 1 hour under reflux at normal pressure conditions. The heating temperature in this acid treatment was from 85 to 100° C. Next, after cooling, the solid content (containing the DND agglutinate and soot) was washed with water by decantation. The solid content was repeatedly washed with water by decantation until the pH of a precipitation liquid reached 2 from the low pH side.

An oxidation treatment was then performed. Specifically, to the precipitation liquid (containing a DND agglutinate) obtained through decantation after the acid treatment, 6 L of a 98 mass % sulfuric acid and 1 L of a 69 mass % nitric acid were added to form a slurry, and then the slurry was subjected to heat treatment under reflux at normal pressure conditions for 48 hours. The heating temperature in this oxidation treatment was from 140 to 160° C. Next, after cooling, the solid content (containing the DND agglutinate) was washed with water by decantation. The supernatant liquid from the initial water washing was colored, and the solid content was repeatedly washed with water by decantation until the supernatant liquid became visually transparent.

Next, the precipitation liquid (liquid containing the DND agglutinate) obtained through the water-washing treatment described above was dried, and a dry powder (DND agglutinate) was obtained. Evaporation to dryness with the use of an evaporator was employed as a technique for the drying treatment in the drying.

Next, 4.5 g of the dry powder (the DND agglutinate) obtained through the drying described above was allowed to stand inside a furnace core tube of a gas atmosphere furnace (trade name "Gas Atmosphere Tube Furnace KTF045N1", available from Koyo Thermo Systems Co., Ltd.), and nitrogen gas was continuously passed through the furnace core tube at a flow rate of 1 L/min for 30 minutes. Then, the flowing gas was switched from nitrogen to a mixed gas of oxygen and nitrogen, and the mixed gas was continuously flowed through the furnace core tube at a flow rate of 1 L/min. The oxygen concentration in the mixed gas is 4 vol. %. After switching to the mixed gas, the temperature inside the furnace was increased to a temperature set for heating of 400° C. The temperature was increased at a rate of 10° C./min to 380° C., a temperature 20° C. lower than the temperature set for heating, and then at a rate of 1° C./min from 380° C. to 400° C. Then, the oxygen oxidation treatment was carried out on the DND powder inside the furnace while the temperature condition inside the furnace was maintained at 400° C. The duration of the treatment was 3 hours.

Next, hydrogenation was performed using the gas atmosphere furnace described above. Specifically, the DND powder subjected to oxygen oxidation was placed inside a gas atmosphere furnace and nitrogen gas was continuously passed through the gas atmosphere furnace at a flow rate of 1 L/min for 30 minutes. Then, the flowing gas was switched from nitrogen to a mixed gas of hydrogen and nitrogen, and the mixed gas was continuously flowed through the furnace core tube at a flow rate of 1 L/min. The hydrogen concentration in the mixed gas was 2 vol. %. After switching to the mixed gas, the temperature inside the furnace was increased to a temperature set for heating of 600° C. The temperature increase rate was 10° C./min. Then, hydrogenation treatment was performed on the DND powder inside the furnace while the temperature inside the furnace was maintained at 600° C. The duration of the treatment was 5 hours. The DND powder subjected to hydrogenation treatment was obtained as described above.

Disintegration was then performed. Specifically, first, 0.9 g of the DND powder subjected to the hydrogenation treatment described above and 29.1 mL of pure water were added to a 50-mL sample bottle and mixed, and about 30 mL of a slurry was obtained. After adjusting the pH to 4 using 1 N hydrochloric acid, the slurry was ultrasonicated. In the ultrasonication, the slurry was irradiated with ultrasonic waves for 2 hours using an ultrasonic irradiator (trade name "Ultrasonic Cleaner AS-3", available from AS ONE Corporation). Thereafter, bead milling was performed using a bead milling apparatus (trade name "Parallel 4-Tube Sand Grinder Model LSG-4U-2L", available from Aimex Co., Ltd.). Specifically, 30 mL of the slurry after the ultrasonic irradiation and zirconia beads with a diameter of 30 μm were charged in a vessel (available from Aimex Co., Ltd.), which was a 100-mL mill vessel, and the vessel was sealed. Then, the apparatus was operated to perform bead milling. In this bead milling, the amount of zirconia beads that were charged was, for example, 33 vol. % of the capacity of the mill vessel, the rotational speed of the mill vessel was 2570 rpm, and the duration of the milling was 2 hours.

Next, the slurry subjected to the disintegration as described above was subjected to centrifugation treatment (a classification operation) using a centrifuge. The centrifugal force in this centrifugation treatment was 20000×g, and the duration of the centrifugation was 10 minutes. Next, 10 mL of supernatant of the DND-containing solution subjected to the centrifugation treatment was collected. A DND dispersion in which the nanocarbon material was dispersed in pure water was thus obtained. This nanocarbon material dispersion had a solid content concentration of 2.1 mass % and a pH of 5.40. The median size (particle size D50) of the DND dispersion obtained as described above was 35.8 nm.

Preparation of DND Surface-Modified with Polyglycerol, "DND-PG"

The DND particle aqueous dispersion obtained through the disintegration described above was concentrated to a solid residue using an evaporator and dried at 105° C. for 2 hours. The resulting DND powder (1.0 g) was suspended in ethylene glycol (15.0 g), glycidol (45.1 g, 0.61 mol) was added dropwise over 105 minutes, and the temperature was maintained in a range from 95 to 102° C. The resulting black dispersion was stirred at the same temperature for 4 hours and then at room temperature overnight. Water (40 mL) was slowly added to decompose the unreacted glycidol, and then the dispersion was diluted with water to 400 mL. The diluted dispersion was then concentrated to 20 mL with an ultrafiltration membrane (Ultracel membrane, 30 kDa). The concentrate was diluted and concentrated again. This was repeated five times to wash the concentrate, and a purified DND-PG as a black aqueous dispersion was obtained. The yield was 100.1 g (the content of the DND-PG was 5.08 mass %, 5.08 g). A portion of the dispersion was dried on a heated PTFE sheet, and a sample for analysis was obtained. The analysis results are shown below.

FT-IR (diffuse reflectance method, $cm^{-1}$): 3332, 2918, 2875, 1458, 1118, 1078 (C—O)

$^1$H-NMR (500 MHz, D20): 6 ppm 3.42, 3.50, 3.58, 3.75, 3.88 ($C_3$ unit)

Elemental analysis: C; 55.72%, H; 7.06%, N; 0.57%, 0; 36.86%

TGA (in air atmosphere, 20° C./min, % weight loss): 383 to 541° C.; 75.4%, 541 to 790° C.; 18.6% (ratio (PG/DND) was presumed to be 4.1)

Figure 2:
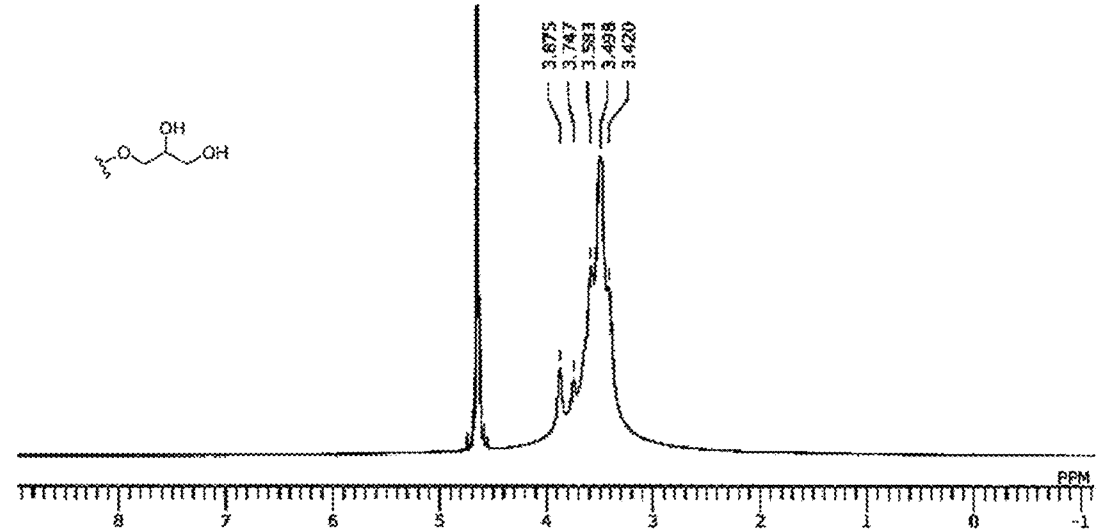
FIG. 2 is a graph showing a $^1$H-NMR spectrum of DND-PG.

The structure of the resulting DND-PG was confirmed by FT-IR and by $^1$H-NMR in a solution, as shown in FIGS. 1 and 2, respectively. In the FT-IR spectrum, absorption due to O—H stretching at 3333 $cm^{-1}$, C—H asymmetric and symmetric stretches at 2918 and 2876 $cm^{-1}$, and C—O—C asymmetric and C—O stretches of the PG chain at 1118 and 1078 $cm^{-1}$ were observed. In the $^1$H-NMR, signals from 3 to 4 ppm indicate that all hydrogen atoms on the PG chain are on carbons adjacent to oxygen-functional groups, such as a hydroxyl group and an ether bond.

Preparation of DND-PG-OTs

The aqueous dispersion (39.4 g) of the DND-PG (content of the DND-PG was 5.08 mass %, 2.0 g) was evaporated to dryness. The residue was dissolved in pyridine (20 mL), and the solution was evaporated to dryness to remove residual water by azeotropic distillation. This operation was repeated once, then the residue was dissolved in pyridine (30 mL), and the solution was ice-cooled. To this solution, p-toluenesulfonyl chloride (Ts-Cl, 3.9 g, 202 mmol) and N,N-dimethylaminopyridine (DMAP, 0.10 g, 0.84 mmol) were added. The reaction mixture was stirred at room temperature for 24 hours. Water (30 mL) was added, and the precipitate was separated by centrifugation at 30000 g for 10 minutes. The precipitate was washed twice with water containing a small amount of tetrahydrofuran (THF) and centrifuged. The precipitate was washed twice with THF-toluene by the same method. The precipitate was vacuum-dried at 40° C., and a black solid was obtained. The yield was 3.91 g. The analysis results are shown below.

FT-IR (diffuse reflectance method, $cm^{-1}$): 3342, 2920, 2878, 1597, 1362, 1177 (SO2), 929, 815, 667, 553

$^1$H-NMR (500 MHz, $CDCl_3$): δ ppm 3.39 to 4.61 ($C_3$ unit), 2.31 ($CH_3$ of -OT), 7.24, 7.67 (aromatic ring of -OT)

Elemental analysis: C; 55.88%, H: 5.30%, N; 0.32%, 0; 27.20%, S; 10.50%

Figure 3:
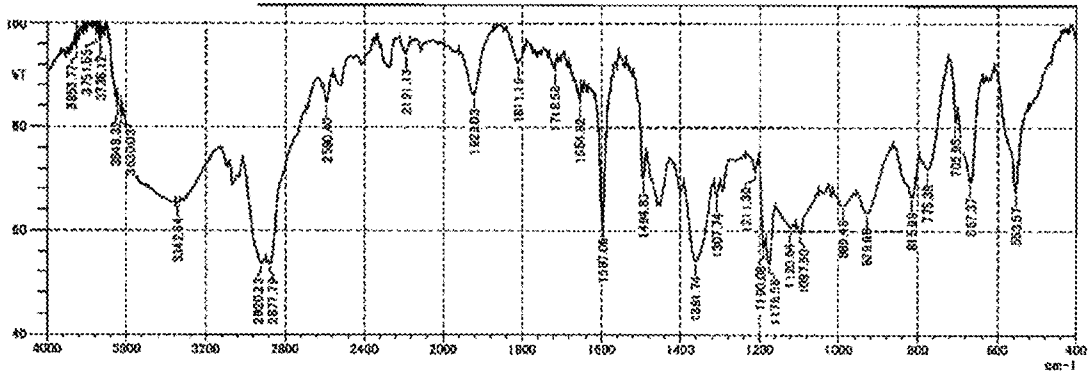
FIG. 3 is a graph showing a FT-IR spectrum of DND-PG-OTs.
Figure 4:
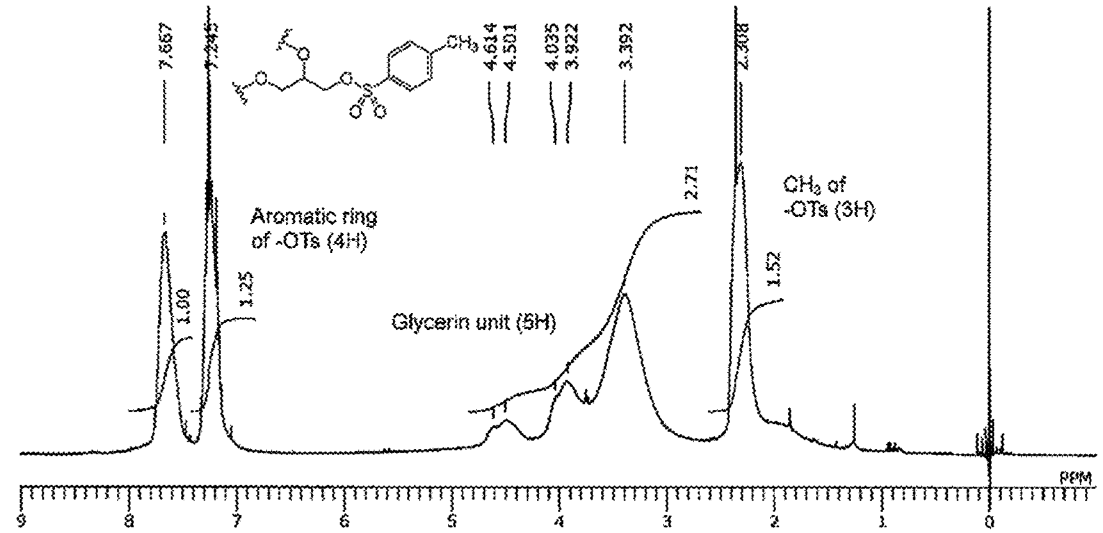
FIG. 4 is a graph showing a $^1$H-NMR spectrum of DND-PG-OTs.

In the resulting DND-PG-OTs, the FT-IR observed peaks at 1362 and 1177 $cm^{-1}$ due to asymmetric and symmetric stretching vibrations of $SO_2$ of the sulfonate ester (FIG. 3). In the $^1$H-NMR, signals of the benzene ring at 7.67 and 7.24 ppm and the methyl group at 2.31 ppm were observed (FIG. 4).

Preparation of DND-PG-$NH_2$·HCl

Figure 5:
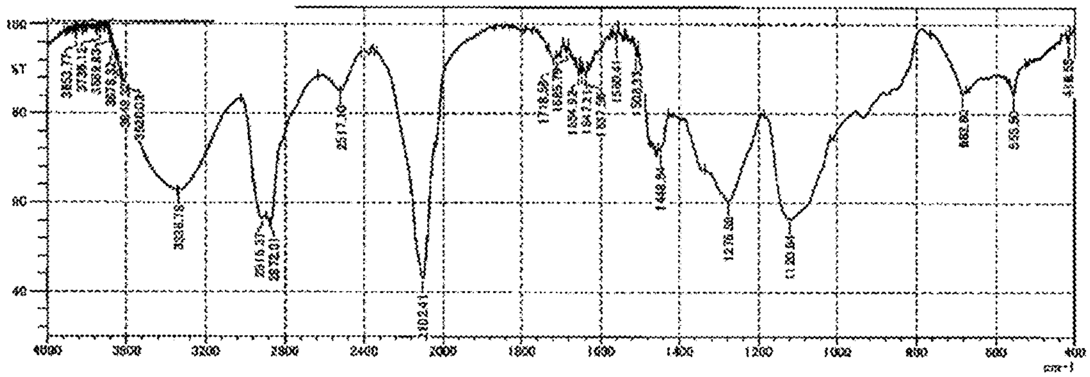
FIG. 5 is a graph showing a FT-IR spectrum of DND-PG-$N_3$.
Figure 6:
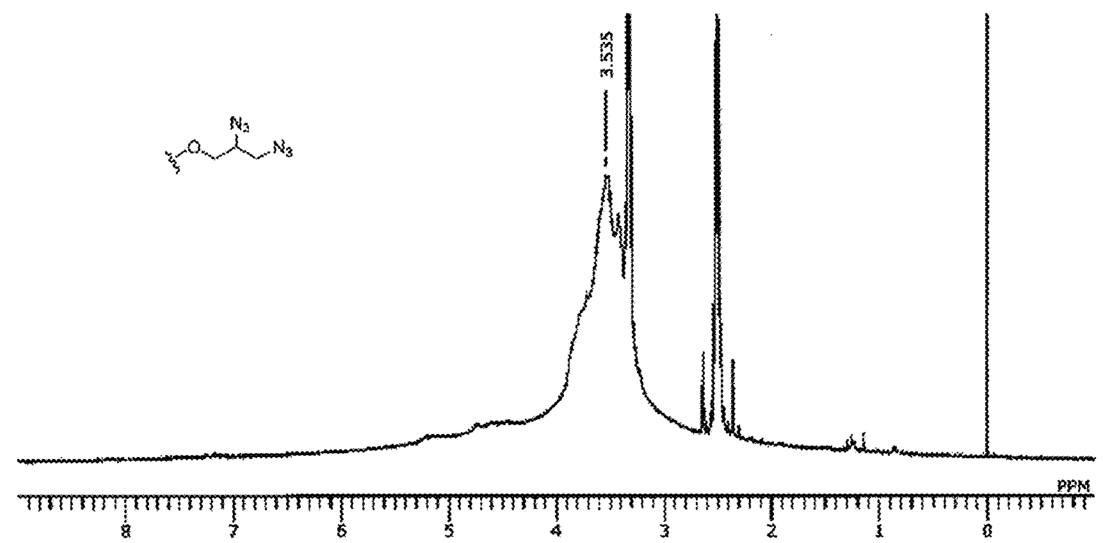
FIG. 6 is a graph showing a $^1$H-NMR spectrum of DND-PG-$N_3$.
Figure 7:
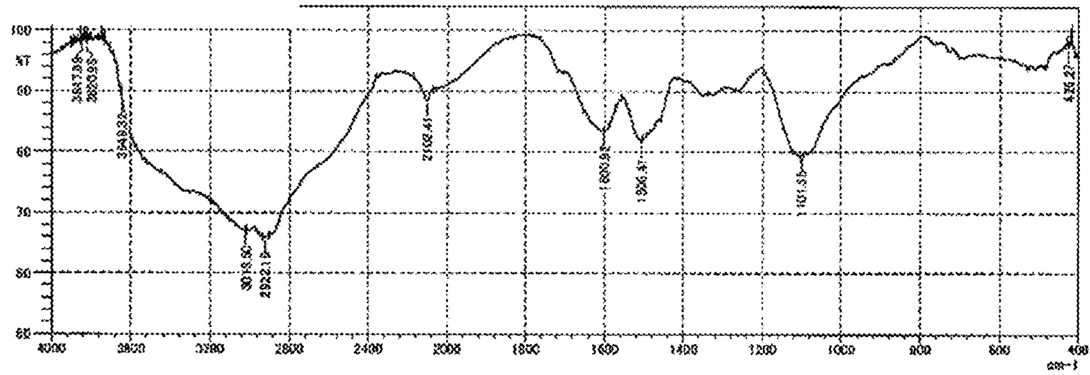
FIG. 7 is a graph showing a FT-IR spectrum of DND-PG-$NH_2$·HCl.
Figure 8:
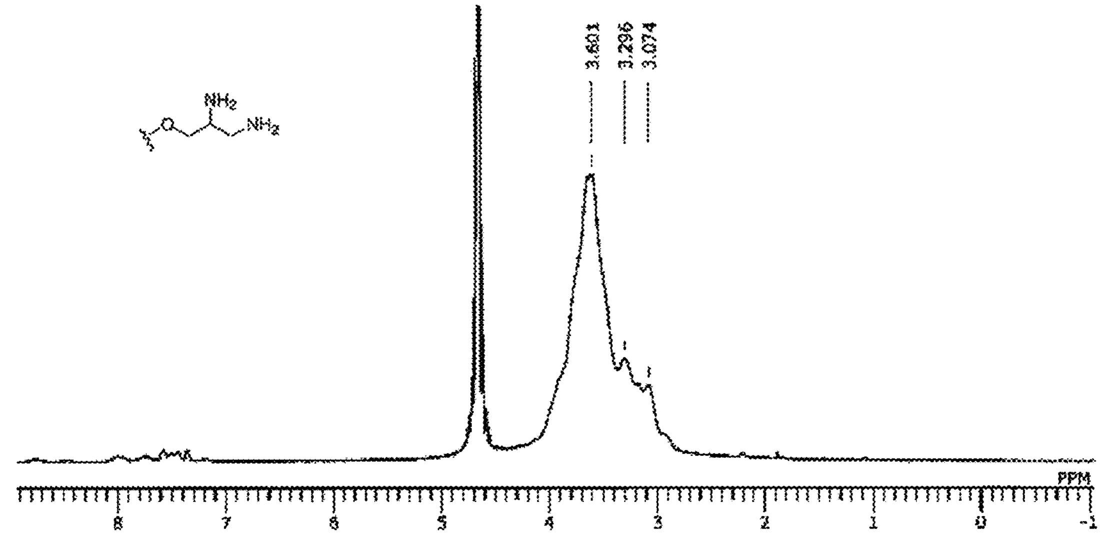
FIG. 8 is a graph showing a $^1$H-NMR spectrum of DND-PG-$NH_2$·HCl.

The tosyl group was then replaced by an azide group, the resulting DND-PG-$N_3$ was reduced to an amino group by the Staudinger reaction with triphenylphosphine ($PPh_3$), and DND-PG-$NH_2$·HCl was obtained. Each structure of DND-PG-$N_3$ and DND-PG-$NH_2$·HCl and the amount of each functional group introduced were confirmed by FT-IR (FIGS. 5 and 7), $^1$H-NMR (FIGS. 6 and 8), and elemental analysis. The specific operation is described below.

Sodium azide ($NaN_3$, 0.66 g, 10.2 mmol) was added to a solution of DND-PG-OTs (2.0 g) in DMF (20 mL). The reactants were stirred at 60° C. for 3 hours and then at 90° C. for 19 hours. Water (20 mL) was added, and the precipitate was separated by centrifugation at 30000 g for 10 minutes. The precipitate was washed twice with water containing a small amount of THF and centrifuged. The precipitate was washed twice with THF-toluene by the same method. The precipitate was vacuum-dried at 40° C., and a black solid was obtained. The yield was 0.67 g. The analysis results are shown below.

FTIR (diffuse reflectance method, $cm^{-1}$): 3338, 2916, 2872, 2102 (azide), 1276, 1120

$^1$H-NMR (DMSO-d6): δ ppm 3.54 ($C_3$ unit)

Elemental analysis: C; 53.59%, H: 5.04%, N; 19.40%, 0; 21.68%

TGA (air atmosphere, 20° C./min, % weight loss): 230 to 587° C.; 71.2%, 587 to 794° C.; 25.9%

DND-PG-$N_3$ (257 mg) was then dissolved in DMF (12 mL), and the solution was ultrasonicated for 15 minutes. Water (1.0 mL), triphenylphosphine ($PPh_3$, 798 mg, 3.00 mmol), and concentrated ammonia water (0.50 mL) were added to the dispersion, and the mixture was stirred at 60° C. for 24 hours. The reaction mixture was concentrated to half volume. After water (10 mL) and 6M HCl (1.0 mL) were added, triphenylphosphine oxide was extracted with ethyl acetate (AcOEt, 20 mL). The aqueous phase was further washed twice with AcOEt, then diluted with water to 400 mL, and concentrated with an ultrafiltration membrane (Ultracel membrane, 30 kDa) to less than 10 mL. The concentrate was diluted and concentrated again. This was repeated twice, and a purified DND-PG-$NH_2$ HCl as a black to dark brown aqueous dispersion was obtained. A portion of the dispersion was dried on a heated PTFE sheet for analysis. The yield was 265 mg. The analysis results are shown below.

FT-IR (drift using KBr, $cm^{-1}$): 3018, 2922, 1601, 1506 (—$NH_2$), 1101

$^1$H-NMR (0.1 M DCl): δ ppm 3.07, 3.30, 3.60 (C3 unit)

Elemental analysis: C; 49.16%, H; 6.69%, N; 6.55%, Cl; 13.49%

TGA (air atmosphere, 20° C./min, % weight loss): 90 to 568° C.; 72.1%, 568 to 800° C.; 26.7%

Preparation of DND-PG-PBA

DND-PG-PBA was introduced by reductive amination of 2-formylphenylboronic acid-$^{10}$B (o-boromobenzaldehyde-$^{10}$B) into DND-PG-$NH_2$.

Preparation of Triisopropyl Borate-$^{10}$B

Boronic acid-$^{10}$B (1.0 g, 16.4 mmol) was added to a mixture of 2-propanol (10 mL) and cyclohexane (30 mL), the mixture was stirred for 30 minutes, and then heated under reflux for 10 minutes. A Dean-Stark apparatus (a receiver was charged with cyclohexane in advance) was attached, and the mixture was refluxed for 6 hours while water and 2-propanol were removed by azeotropic distillation until the vapor temperature reached 80° C. The solvents were removed, and the residue (3.46 g) was used in the next reaction without further purification.

Preparation of 2-formylphenylboronic acid-$^{10}$B 2-(2-Bromophenyl)-1,3-dioxolane (1.30 g, 5.7 mmol) was dissolved in anhydrous diethyl ether (10 mL) under a nitrogen atmosphere, and the solution was cooled to −78° C. An n-hexane solution of n-butyllithium (1.6 M, 3.9 mL, 6.24 mmol) was slowly added, and the mixture was stirred at −78° C. for 1 hour. Triisopropyl borate-$^{10}$B (crude product 1.69 g, prepared from 8.2 mmol of boric acid-$^{10}$B) was added to a suspension of lithium salt at −78° C., and the mixture was stirred at −60° C. or lower for 3 hours and then stirred at room temperature overnight. Water (20 mL), methyl t-butyl ether (MTBE, 20 mL), and 2.5 M (10 mass %) NaOH (5.0 mL) were added, and the phases were separated. The aqueous phase was washed twice with MTBE and then acidified with 6 M HCl (5.0 mL). Precipitated oil was extracted three times with MTBE, and the combined organic phase was dried over anhydrous $MgSO_4$. After the $MgSO_4$ was filtered off, the organic phase was concentrated under reduced pressure. The crude product was recrystallized from MTBE and n-hexane, and an off-white crystalline powder was obtained. The yield was 0.50 g (59 mass %). The analysis results are shown below.

FT-IR (diffuse reflectance method, $cm^{-1}$): 3346, 3072, 1670, 1490, 1463, 1427, 1384 ($^{10}$B—O), 1195, 858, 765, 748, 648

$^1$H-NMR (methanol-d4): 6.00, 7.42, 7.47, 7.59, 7.67, 7.92, 9.96 (mixture of two tautomers)

ESI-MS (Nagative, m/z): Anal. 148.08818 (M-H$^-$); Calc. $C_7H_6BO_3$ 148.0441

Figure 9:
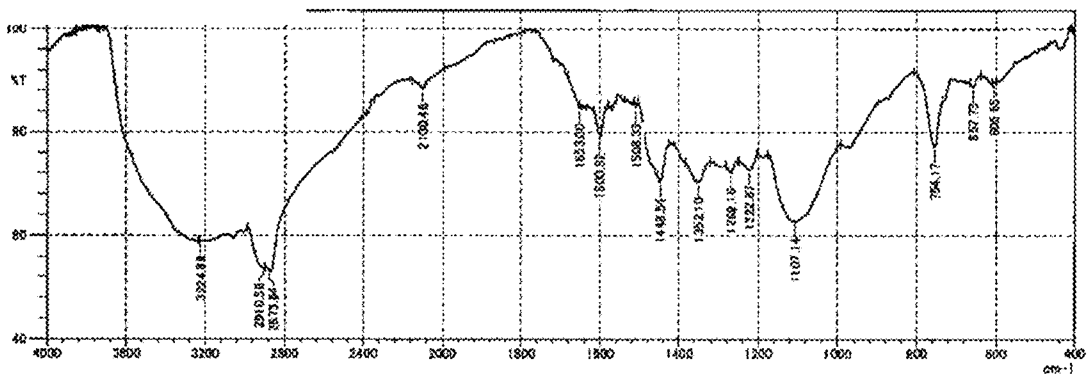
FIG. 9 is a graph showing a FT-IR spectrum of DND-PG-PBA.
Figure 10:
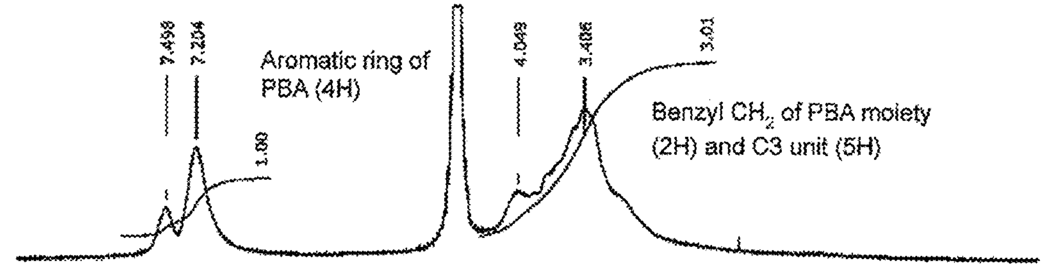
FIG. 10 is a graph showing a $^1$H-NMR spectrum of DND-PG-PBA.

A one pot reaction was performed, in which DND-PG-$NH_2$ was reacted with 2-formylphenylboronic acid-$^{10}$B in methanol to form the corresponding imine and then the imine was reduced with $NaBH_4$. 2-Formylphenylboronic acid-$^{10}$B, which has a boronic acid group enriched in $^{10}$B, is easily synthesized from commercially available $^{10}$B boronic acid via its triisopropyl ester. The presence of the PBA structure in the resulting product (DND-PG-PBA) was confirmed by absorptions at 1352 and 754 $cm^{-1}$ corresponding to BO stretching and out-of-plane bending of the 1,2-disubstituted benzene ring in the FT-IR spectrum (FIG. 9). In the $^1$H-NMR, signals derived from the benzene ring at 7.50 and 7.20 ppm, and a signal derived from a benzylic proton of PBA at 4.05 ppm were observed (FIG. 10).

Preparation of DND-PG-PBA

The aqueous dispersion of DND-PG-$NH_2$ HCl (net 108 mg) was evaporated to dryness under reduced pressure. The residue was dispersed in methanol, then ethanol was added and the mixture was evaporated to dryness. Methanol (10 mL) was added to the residue, and the mixture was ultrasonicated for 30 minutes. 2-Formylphenylboronic acid-$^{10}$B (50.4 mg, 0.34 mmol), triethylamine (145 mg, 1.43 mmol), and anhydrous magnesium sulphate ($MgSO_4$, 254 mg) were added, and the mixture was stirred at 60° C. for 19 hours. The reaction mixture was cooled to 0° C. in an ice-bath, sodium borohydride ($NaBH_4$, 119 mg, 3.20 mmol) was added in two portions over 2 hours, and then the mixture was stirred at 60° C. for 6 hours. The reaction mixture was concentrated to remove methanol, and water (10 mL) and 6M HCl (5.0 mL) were added. The precipitate was separated by centrifugation at 30000 g for 20 minutes and dissolved again in water (8 mL). After 6M HCl (2.0 mL) was added, the mixture was stirred at 100° C. for 2.5 hours. The reaction mixture was concentrated by ultrafiltration (AmiconUltra, 10 kDa, 3300 rpm, 30 min). An operation of washing the material on the membrane with water by dilution followed by ultrafiltration was performed four times. The concentrate on the filter was diluted with water (6.0 g after dilution), and then the pH was adjusted to 7.4. Thereafter, washing by ultrafiltration was further performed four times. To prepare an analytical sample, the resulting dispersion was freeze-dried, and DND-PG-PBA as an off-white powder was obtained. The yield was 104 mg (net). The analysis results are shown below.

FT-IR (diffuse reflectance method, $cm^{-1}$): 3224, 2910, 2873, 1448 (B—N), 1352 (B—O), 1107, 754 (1,2-disubstituted benzene)

$^1$H-NMR (0.1 M DCl): δ ppm 7.50, 7.20 (aromatic ring of PBA), 4.05, 3.41 (benzylic positions of PBA and $C_3$ unit)

Elemental analysis: C; 60.11%, H: 6.14%, N; 5.51%

The amount of PBA groups introduced into DND-PG-PBA obtained by the reaction with DND-PG-$NH_2$·HCl ($NH_2$ group content: 4.22 mmol/g) and 2-formylphenylboronic acid-$^{10}$B (3.15 mmol per g of DND-PG-$NH_2$·HCl) was calculated to be 2.24 mmol/g from the results of elemental analysis (Table 1).

TABLE 1

Amount of PBA based on the change of nitrogen content

| | DND-PG-$NH_2$•HCl | DND-PG-PBA |
|---|---|---|
| Carbon content by EA[a] (wt %) | 49.10 | 60.11 |
| Nitrogen content by EA (wt %) | 6.55 | 5.51 |
| Carbon from DND-PG-$NH_2$•HCl (wt %) | 49.10 | 41.30[b] |
| Carbon from PBA moiety (wt %) | | 18.81 |
| Amount of PBA (mmol/g) | | 2.24 |
| Amount of PBA (g/g) | | 0.300 |
| Amino group content (mmol/g) | 4.22 | 3.55 |
| Unreacted amino group (mmol/g) | | 1.31 |

[a]elemental analysis

[b]Calculated by "C in DND-PG-$NH_2$•HCl"/"N in DND-PG-$NH_2$•HCl" × "N in DND-PG-PBA".

DND-PG-PBA exhibited dispersibility in phosphate buffered saline (PBS) at 50 mg/mL. Such high dispersibility is probably due to the "Wulff-type PBA", in which the nitrogen atom of the aminomethyl group at the ortho position coordinates with the boron atom of the boronic acid moiety to give a five-membered ring. That is, phenylboronic acid and the aminomethyl group are considered to form a five-membered ring structure that satisfies the Wulff pattern and thus lower the pKa (that is, increase affinity with water) and increase dispersibility.

Preparation of DND-PG-PBA-Suc and DND-PG-PBA-SucMe

The amino groups were converted to amides by succinylation and to methylamino groups by methylation. Some secondary amino groups were intentionally not succinylated to enable Wulff-type coordination and were then methylated. About 2 mmol of succinic anhydride was used per g of DND-PG-PBA. Furthermore, the remaining secondary amino groups were methylated by reductive amination with formaldehyde.

Preparation of DND-PG-PBA-Suc

To 21 g of an aqueous dispersion of DND-PG-PBA (content of DND-PG-PBA 180 mg, pH 3.59), succinic anhydride (39.1 mg, 0.390 mmol) was added in several portions over 2 hours while the pH was adjusted to 8.0 to 9.5 using 1M NaOH. The reaction mixture was then at pH 8.4 and stirred at room temperature overnight. Some of the reaction mixture (6.0 g of 24.0 g) was washed by performing an operation of diluting the mixture with water followed by ultrafiltration five times, and a partially succinylated material was obtained. The yield was 45.1 mg, or 180 mg as the whole reaction liquid. The analysis results are shown below.

FT-IR (diffuse reflectance method, $cm^{-1}$): 3275, 2916, 2874, 1654 (amide C═O), 1570, 1448, 1394, 1363, 1112, 754

$^1$H-NMR (0.1 M DCl): 6 ppm 7.57, 7.25 (aromatic ring of PBA), 4.08, 3.34 (benzylic positions of PBA and $C_3$ unit), 2.35 (succinyl)

Elemental analysis: C; 57.62%, H: 6.27%, N; 5.77%

Preparation of DND-PG-PBA-SucMe

Some of the reaction mixture of DND-PG-PBA-Suc (18.0 g of 24.0 g, containing 135 mg of DND-PG-PBASuc) was ice-cooled. After a formaldehyde solution (HCHO, 36%, 0.80 mL) and $NaBH_4$ (136.3 mg, 3.67 mmol) were added, the reaction mixture was stirred at room temperature overnight. After 6 M HCl (3.0 mL) was added with care for foaming, the mixture was stirred at 80° C. for 2 hours. After the mixture was diluted with water and washed by ultrafiltration, the pH was adjusted to about 7.0 with 1 M NaOH. A small amount of succinic anhydride (7.6 mg in total) was added in several portions, and the resulting material was found to be dispersible at a pH of 6.9 or higher. The pH was adjusted to 7.4, and the resulting solution was washed several times by ultrafiltration (Ultracel membrane, 30 kDa and AmiconUltra, 10 kDa). The yield was 135 mg. The analysis results are shown below.

FT-IR (diffuse reflectance method, $cm^{-1}$): 3280, 2926, 2878, 1653, 1568, 1446, 1394, 1362, 1109, 756

$^1$H-NMR (0.1 M DCl): 6 ppm 7.56, 7.25 (PBA), 4.08, 3.34 (benzylic positions of PBA and $C_3$ unit), 2.67 (N—$CH_3$), 2.33 (succinyl group (—$CH_2CH_2$—))

Elemental analysis: C; 56.60%, H; 6.36%, N; 5.83%. Boron content (ICP-AES): 1.85%

Preparation of DND-PG-FPBA, DND-PG-FPBA-Suc and DND-PG-FPBA-SucMe

DND-PG-FPBA, DND-PG-FPBA-Suc, and DND-PG-FPBA-SucMe were prepared in the same manner as in the preparation method of DND-PG-PBA and the like except that FPBA was used instead of PBA. For samples for biological experiments, the solution was concentrated by ultrafiltration, diluted with water as necessary, and filtered through a 0.45-μm membrane. Then, 10×PBS(−) or PBS(−) was added to prepare a target concentration and isotonicity.

Preparation of 2-formyl-3-fluorophenylboronic acid-$^{10}$B "FPBA"

2-Bromo-6-fluorobenzaldehyde (0.93 g, 4.6 mmol) was dissolved in methanol (10 mL), trimethyl orthoformate (1.56 g, 14.7 mmol) and p-toluenesulfonic acid monohydrate (23.7 mg, 0.12 mmol) were added, and the mixture was heated under reflux for 2 hours. Methanol was evaporated under reduced pressure, toluene and a saturated $NaHCO_3$ aqueous solution were added to the residue, and the layers were separated. The organic layer was washed with saturated saline, and dried over anhydrous $MgSO_4$. The drying agent was filtered off, and the filtrate was concentrated under reduced pressure. The resulting colorless liquid (1.18 g) was used for the next operation without further purification. The 2-bromo-6-fluorobenzaldehyde dimethyl acetal (1.18 g) was dissolved in anhydrous diethyl ether (10 mL) under a nitrogen atmosphere, and the solution was cooled to −78° C. An n-hexane solution of n-butyllithium (1.6 M, 3.75 mL, 6.0 mmol) was slowly added, and the mixture was stirred at −78° C. for 1 hour. Triisopropyl borate-$^{10}$B (crude product 1.69 g, prepared from 8.2 mmol of boric acid-$^{10}$B) was added to a suspension of the lithium salt at −78° C. The mixture was stirred at −60° C. or lower for 1 hour and then stirred at room temperature for 4 hours. Water (20 mL), methyl t-butyl ether (MTBE, 20 mL), and 2.5 M (10 mass %) NaOH (5.0 mL) were added, and the phases were separated. The aqueous phase was washed twice with MTBE and then acidified with 6 M HCl (5.0 mL). Precipitated oil was extracted three times with MTBE, and the combined organic phase was dried over anhydrous $MgSO_4$. After the $MgSO_4$ was filtered off, the organic phase was concentrated under reduced pressure. To the residue (0.73 g), THF (5 mL), water (5 mL), and p-toluenesulfonic acid monohydrate (45.2 mg, 0.24 mmol) were added, and the mixture was stirred at room temperature overnight. THF was evaporated under reduced pressure, MTBE was added to the residue, and the layers were separated. The organic layer was washed twice with saturated saline, and the mixture was dried over anhydrous $MgSO_4$. After the $MgSO_4$ was filtered off, the organic layer was concentrated under reduced pressure. The crude product was recrystallized from MTBE and n-hexane, and an off-white crystalline powder was obtained. The yield was 0.29 g (38%). The analysis results are shown below.

$^1$H-NMR ($CDCl_3$): 6.96 (2H, B—$(OH)_2$), 7.70 (1H), 7.99 (1H), 7.28 (1H), 10.46 (1H, CHO)

ESI-MS (Nagative, m/z): Anal. 166.07884 (M-$H^-$); Calc. $C_7H_5BFO_3$ 167.04

Figure 22:
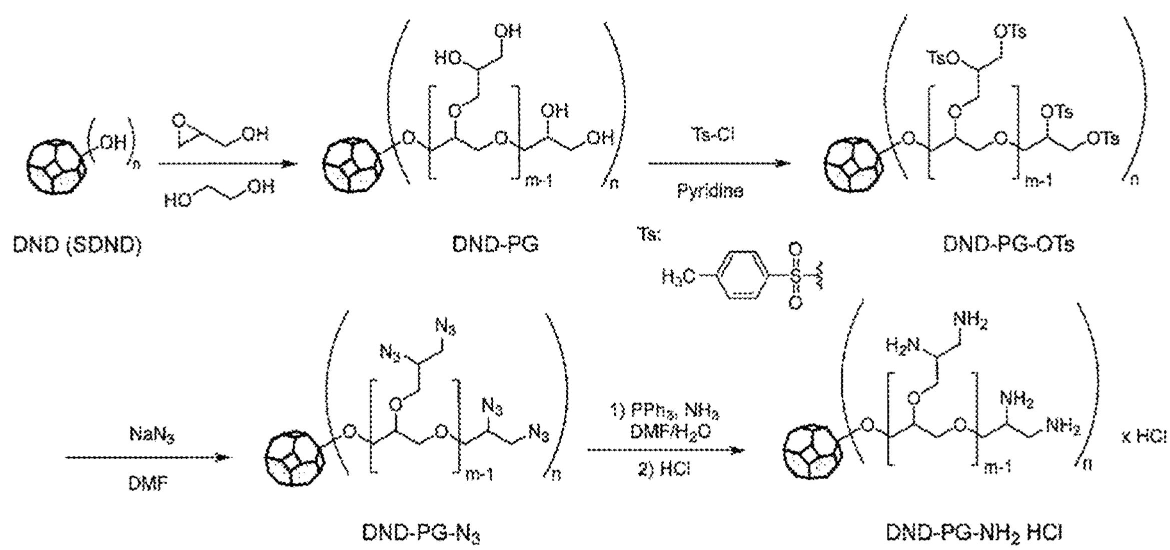
FIG. 22 is a diagram illustrating a synthesis scheme from DND to DND-PG-$NH_2$·HCl.
Figure 23:
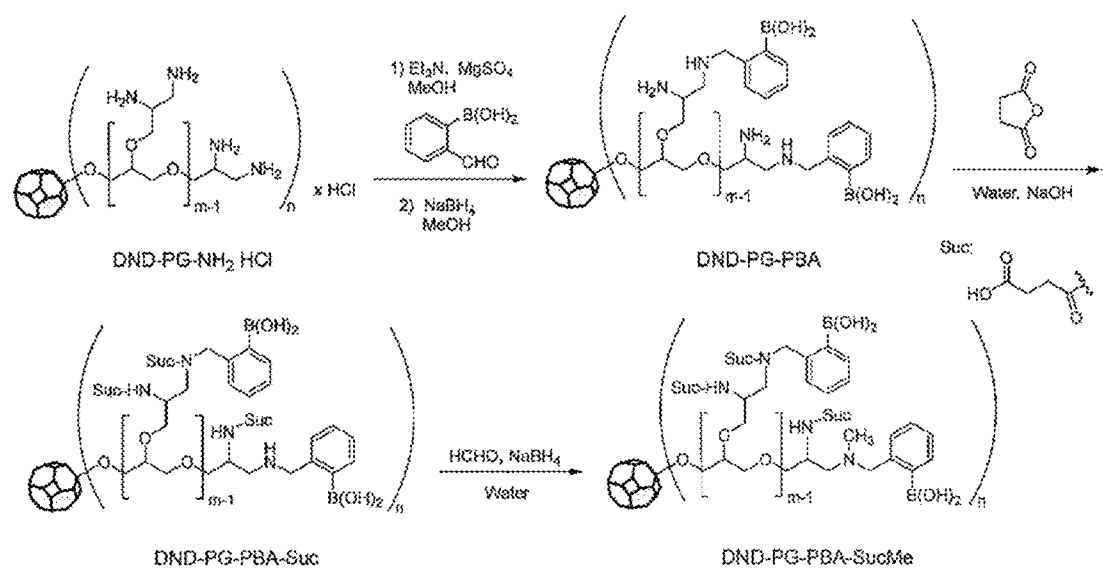
FIG. 23 is a diagram illustrating a synthesis scheme from DND-PG-$NH_2$·HCl to DND-PG-PBA-SucMe.

The reaction scheme from DND to DND-PG-PBA-SucMe is shown in FIGS. 22 and 23.

Figure 11:
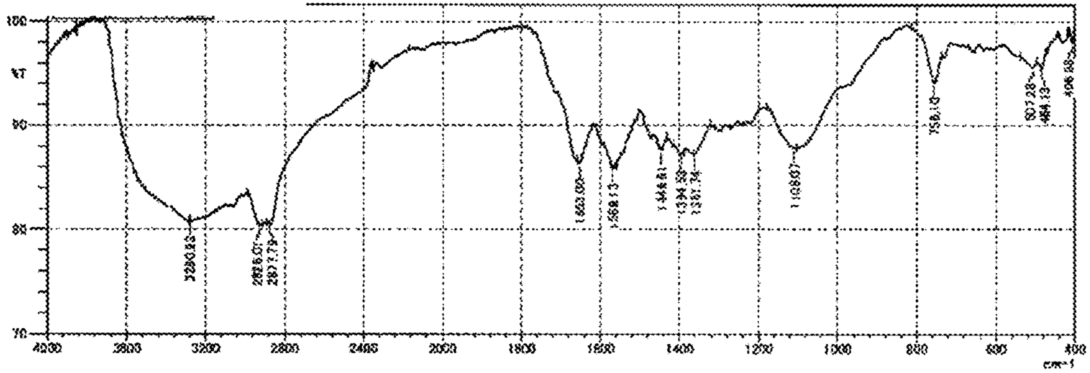
FIG. 11 is a graph showing a FT-IR spectrum of DND-PG-PBA-Suc.
Figure 12:
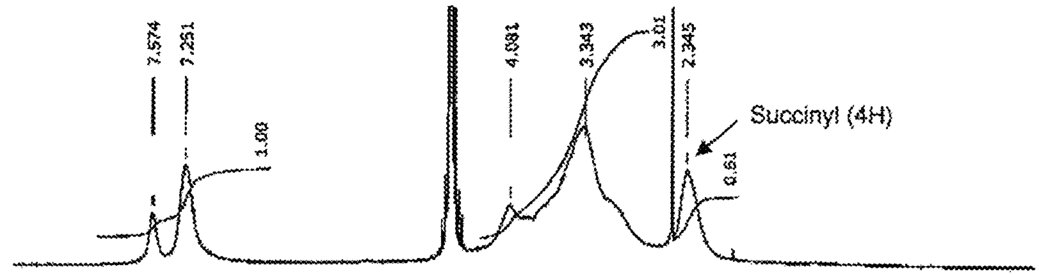
FIG. 12 is a graph showing a $^1$H-NMR spectrum of DND-PG-PBA-Suc.
Figure 13:
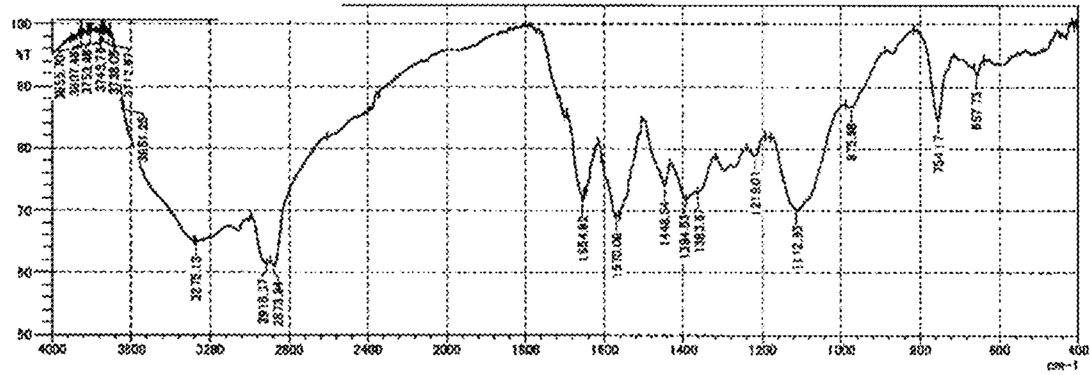
FIG. 13 is a graph showing a FT-IR spectrum of DND-PG-PBA-SucMe.
Figure 14:
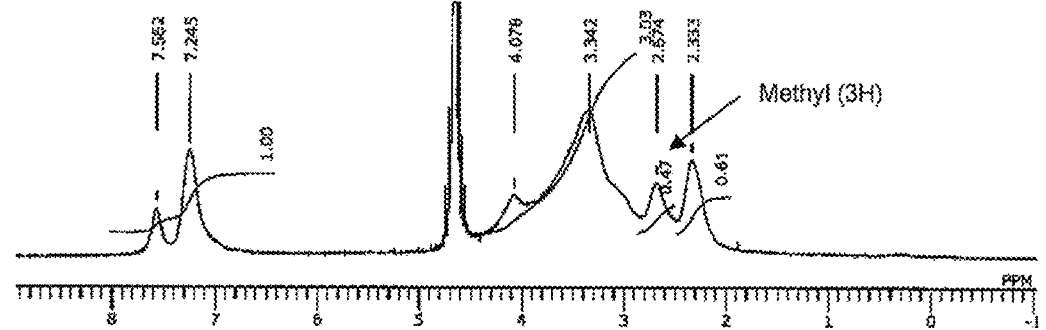
FIG. 14 is a graph showing a $^1$H-NMR spectrum of DND-PG-PBA-SucMe.

In the FT-IR of DND-PG-PBA-Suc (FIG. 11), peaks of C═O stretching vibrations of amide and carboxylate (—COO—) were observed at 1653 and 1568 $cm^{-1}$, respectively. In the $^1$H NMR spectrum (FIG. 12), a signal at 2.34 ppm was assigned to the hydrogens of the succinyl moiety (—$CH_2CH_2$—). FIGS. 13 and 14 are FT-IR and $^1H$ NMR spectra of DND-PG-PBA-SucMe after methylation. In DND-PG-PBA-SucMe, a new signal appeared at 2.67 ppm corresponding to a methyl group in the $^1H$ NMR. The amounts of succinyl groups and methyl groups carried were estimated from the integrated values of $^1H$ NMR. The succinyl groups in DND-PG-PBA-Suc were 1.20 mmol/g, and the succinyl groups and methyl groups in DND-PG-PBA-SucMe were 1.17 mmol/g and 1.20 mmol/g, respectively. The boron content in DND-PG-PBA-SucMe according to ICP-AES was 1.85 mass %. The boron content determined by the content of PBA groups was 2.06 mass %. The amount of each functional group in each material was summarized in Table 2.

TABLE 2

Content of functional groups in DND-PG derivatives

| | Functional group content (mmol/g) | | | | | | Boron content[a] |
|---|---|---|---|---|---|---|---|
| | OTs | $N_3$ | $NH_2$ | PBA | Succinyl | Methyl | (%) |
| DND-PG-OTs | 3.28 | | | | | | |
| DND-PG-$N_3$ | | 4.45 | | | | | |
| DND-PG-$NH_2$•HCl | | | 4.22 | | | | |
| DND-PG-PBA | | | 1.31 | 2.24 | | | 2.42 |
| DND-PG-PBA-Suc | | | | 1.97 | 1.20 | | 2.13 |
| DND-PG-PBA-SucMe | | | | 1.91 | 1.17 | 1.20 | 2.06 (1.85[b]) |

[a]Calculated value from the molar ratio of PBA moiety.
[b]Result from ICP-AES.

Cytotoxicity Evaluation

Figure 15:
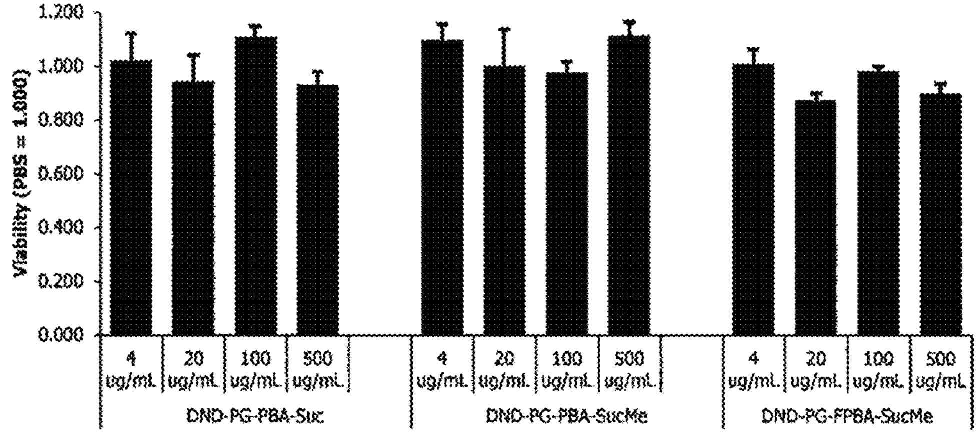
FIG. 15 is a graph related to evaluation of cytotoxic activity of DND-PG-PBA-Suc, DND-PG-PBA-SucMe, and DND-PG-FPBA-SucMe.

The cytotoxicities of DND-PG-PBA-Suc, DND-PG-PBA-SucMe, and DND-PG-FPBA-SucMe were evaluated (FIG. 15). For the tumor model, CT26 mouse colon tumor cells were used. None of the surface-modified DND particles exhibited toxicity even at a relatively high concentration (500 μg/mL). The specific operation of evaluation was as follows.

CT26 mouse colon tumor cells suspended in RPMI 1640 medium (containing 10 vol. % of fetal bovine serum (FBS) and 1 vol. % of a 100× penicillin-streptomycin-amphotericin B solution) were seeded in a 96-well microplate at $4\times10^3$ cells per well (160 μL). After culturing in a $C_{02}$ incubator at 37° C. for 24 hours, the medium was changed once, and PBS or a PBS solution of the nanoparticle (4, 20, 100, or 500 μg/mL, 40 μL each) was added to the medium. After 24 hours of incubation, the medium was changed, and the cells were incubated for another 48 hours. The cells were washed with PBS, then CCK-8 in a culture solution (a mixed solution of 2-(2-methoxy-4-nitrophenyl)-3-(4-nitrophenyl)-5-(2,4-disulfophenyl)-2H-tetrazolium, monosodium salt (WST-8) and 1-methoxy-5-methylphenazinium methylsulfate (1-methoxy PMS), Dojindo Laboratories, 10 μL of CCK-8 and 100 μL of the medium) was added. After 1.5 hours, the absorbance at 450 nm of each well was measured using a microplate reader.

Pharmacokinetic Evaluation

Figure 16:
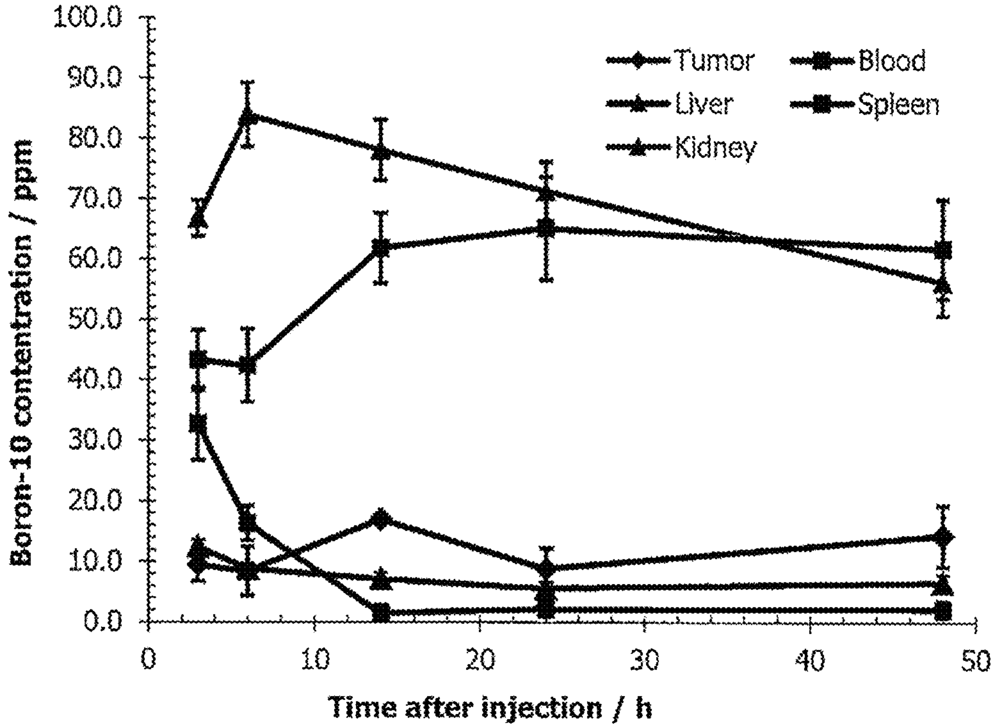
FIG. 16 is a graph related to pharmacokinetics of DND-PG-PBA-SucMe.

To determine the timing of drug injection before neutron irradiation, pharmacokinetics was evaluated. No acute symptoms were observed in mice at the time of sample injection. The pharmacokinetic results are shown in FIG. 16. The specific operation of evaluation was as follows.

BALB/c mice (female, 6 weeks old) were raised. CT26 tumor cells were implanted subcutaneously into the right thigh of the BALB/c mice (female, 6 weeks old) ($1\times10^6$ cells per mouse) one week before sample injection. The mice were injected intravenously with a solution of DND-PG-PBA-SucMe-$^{10}B$ in PBS (4.0 mass %, 200 μL per mouse). After 0.5, 3, 6, 14, 24, and 48 hours, the mice were sacrificed, and the tumor, blood, liver, spleen, and kidney were extracted and placed in individual PTFE tubes. The $^{10}B$ concentration in each sample was measured by neutron-induced prompt gamma-ray analysis (PGA) using equipment installed in a Kyoto University Reactor (KUR).

Figure 18:
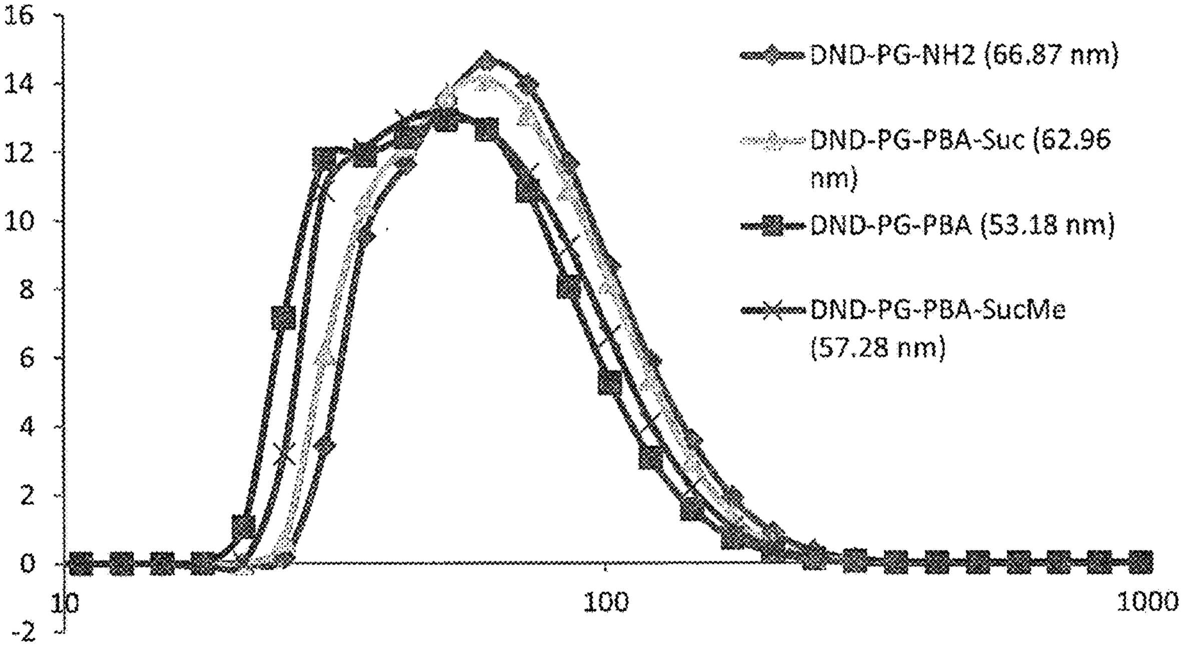
FIG. 18 is a graph related to hydrodynamic size of each material, such as DND-PG-$NH_2$, by DLS.

Hepatic and splenic $^{10}B$ concentrations were higher than blood, tumor, and renal $^{10}B$ concentrations from 3 to 48 hours after injection, indicating that DND-PG-PBA-SucMe tends to accumulate in these organs. On the assumption that the average weight of the liver is 0.96 g and that of the spleen is 0.08 g, not less than half of the injected surface-modified DND particles is calculated to have accumulated in these organs. Although PG has been reported to avoid accumulation in the liver and spleen (stealth effect), the PBA and/or SucMe moieties possibly reduced the efficiency. On the other hand, renal $^{10}B$ concentration was low, meaning that the hydrodynamic diameter obtained by DLS was larger than 20 nm and thus DND-PG-PBA-SucMe was not excreted from the kidney (FIG. 18).

Figure 17:
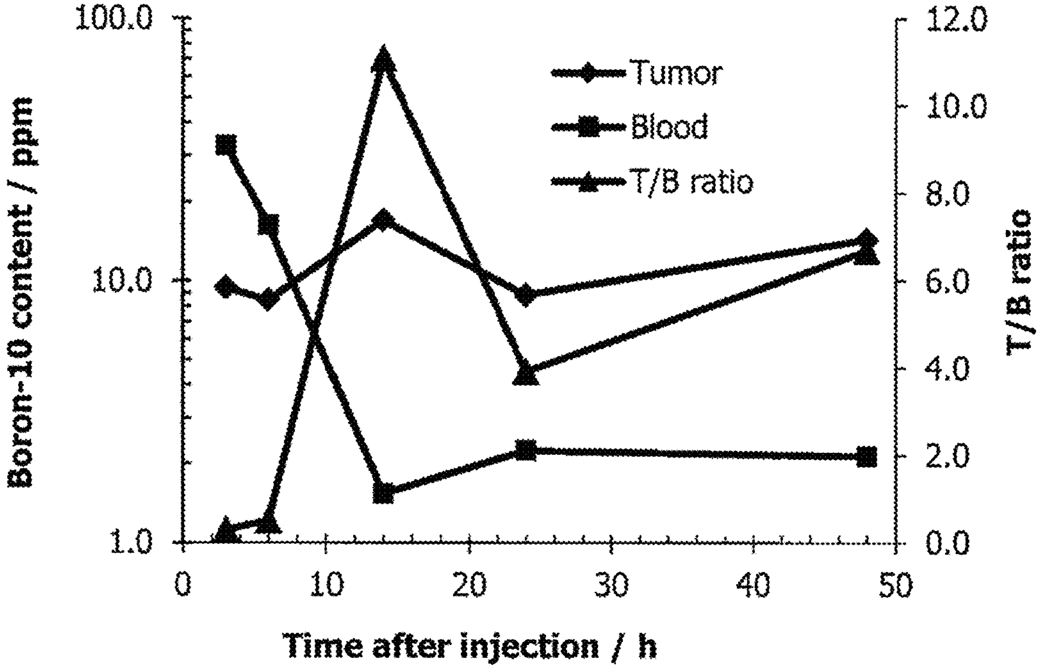
FIG. 17 is a graph related to $^{10}$B concentrations in a tumor and blood, and a ratio of these (T/B ratio).

To determine BNCT conditions, $^{10}B$ concentrations in the tumor and blood and the ratio of these (T/B ratio) are shown in FIG. 17. In addition to the accumulation of the drug in the tumor at high concentration aiming at a high BNCT effect, safety also needs to be considered to avoid side effects. In addition to the toxicity of the surface-modified ND evaluated in the in vitro experiment described above, the T/B ratio is an important indicator. The $^{10}B$ concentration in the tumor was 17.1 ppm at 14 hours and 14.3 ppm at 48 hours, which was higher than at other time points. The $^{10}B$ concentration in blood decreased from 32.8 ppm at 3 hours with a half-life of about 3 hours, and the T/B ratio was 11.1 at 14 hours and 6.7 at 48 hours, which was higher than at other time points. The T/B ratio for a safe level of BNCT exceeded 3, and thus neutron irradiation was applied about 14 and 48 hours after injection of DND-PG-PBA-SucMe.

BNCT Test

BALB/c mice were injected with a PBS dispersion of DND-PG-PBA-SucMe in the same manner as in the pharmacokinetic experiment and irradiated with neutrons after 16 hours and after 48 hours. The specific operation is as follows.

BALB/c mice (female, 6 weeks old) were raised. CT26 tumor cells were implanted subcutaneously into the right thigh of the BALB/c mice ($1\times10^6$ cells per mouse) one week before neutron irradiation. The mice were injected intravenously with a DND-PG-PBA-SucMe-$^{10}$B sample solution in PBS (4.0 mass %, 200 μL per mouse) 16 hours before and 48 hours before neutron irradiation (5 mice per group). Mice were also prepared for an injection control group (with sample injection and without irradiation), a hot control group (with irradiation and without sample injection), and a cold control group (without treatment). At the time of neutron irradiation, the mice were anesthetized and individually held in an acrylic tube holder with the tumor-bearing thigh and leg extended, allowing only the tumor site to be exposed to neutrons. The tube holders were radially fixed on an acrylic plate (12 mice per plate), and the tumor sites were centered. Other parts of the mice were covered with a shield plate to prevent neutron exposure. The tumors were irradiated with neutrons for 10 minutes. The fluence of the neutrons was either $3.99\times10^{12}$ or $3.55\times10^{12}$ neutrons/$cm^2$ (the mice were separated into two irradiation batches). The irradiated mice were kept in a radiation-controlled area for a designated period of time. Changes in the tumor size and body weight were monitored periodically. For the tumor size, the dimensions of two axes of an elliptical tumor were measured with a caliper. Tumor volume was calculated as "volume=(major axis×minor axis$^2$)/2", where the major axis was the longer dimension of the tumor (externally observed as an ellipse), and the minor axis was the shorter dimension.

Figure 19:
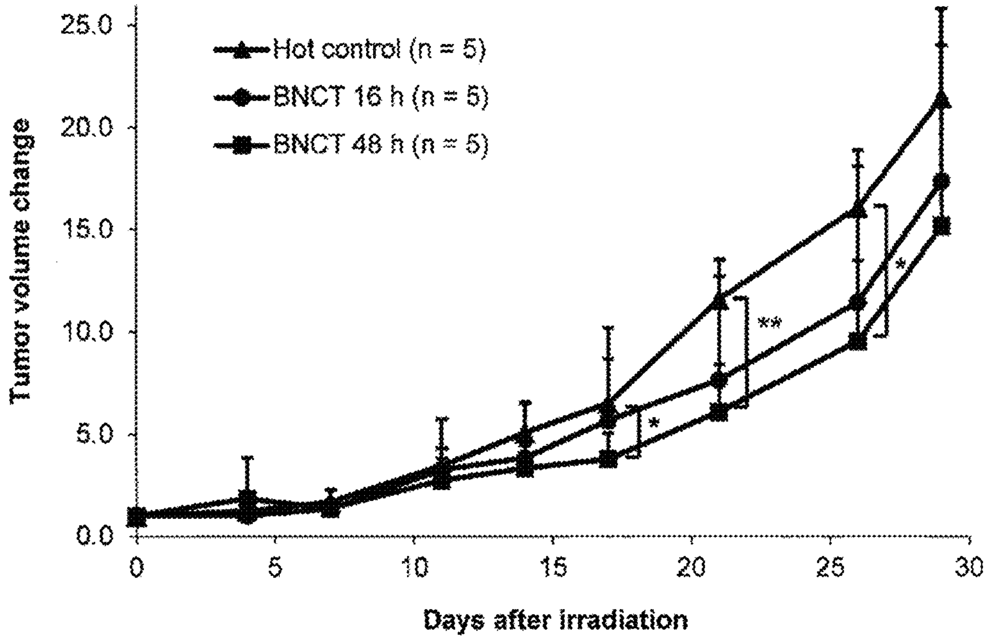
FIG. 19 is a graph showing results of monitoring tumor size for 29 days after BALB/c mice were injected with DND-PG-PBA-SucMe and irradiated with neutrons.
Figure 20:
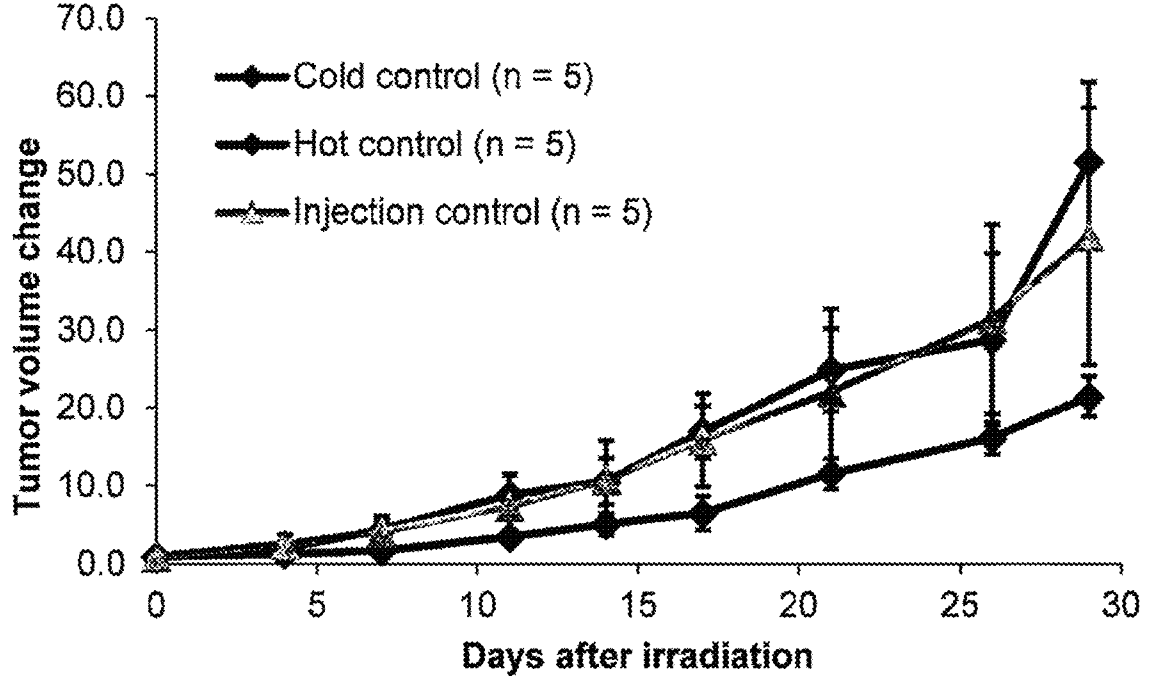
FIG. 20 is a graph showing results of monitoring tumor size for 29 days after BALB/c mice were injected with DND-PG-PBA-SucMe and irradiated with neutrons.
Figure 21:
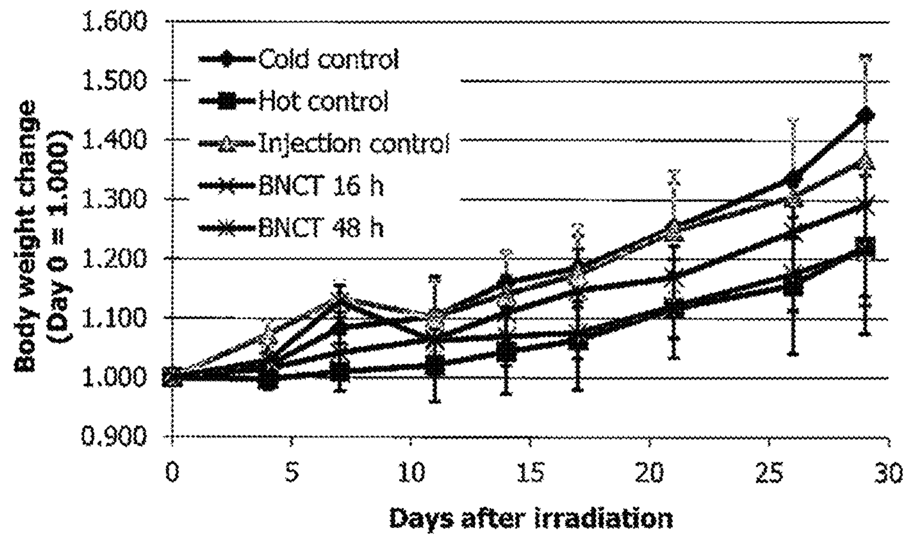
FIG. 21 is a graph showing results of monitoring body weight for 29 days after BALB/c mice were injected with DND-PG-PBA-SucMe and irradiated with neutrons.

The results of monitoring the tumor size and body weight for 29 days after neutron irradiation are shown in FIGS. 19 to 21. The surface-modified ND itself did not affect the tumor growth (injection control in FIG. 20). Even when no surface-modified ND was injected, neutron irradiation showed a certain extent of tumor growth inhibition (hot control in FIG. 20). Compared with the hot control group, the BNCT group administered with DND-PG-PBA-SucMe showed a statistically significant BNCT effect 17, 21, and 26 days after neutron irradiation (BNCT 48 h in FIG. 19). No significant difference was observed with regard to body weight between the hot control group and the BNCT group, indicating no acute or subacute toxicity of the surface-modified ND (FIG. 21). Reproducibility with an experiment using a small number of mice (n=2, 3) was also confirmed, concluding that DND-PG-PBA-SucMe is a promising surface-modified ND for BNCT.

In addition, although some aggregation of DND-PG-PBA was observed in the PBS mixture of fetal bovine serum (FBS), no aggregation of DND-PG-PBA-Suc and DND-PG-PBA-SucMe was observed. The specific method for determining the aggregation was as follows.

When 0.5 parts by mass of the surface-modified nanodiamond was blended with 99.5 parts by mass of a PBS (pH 7.4)/FBS (45/55 (v/v)) solution and the solution was stored at 25° C., whether an aggregate substantially formed within 10 minutes was visually determined. The fetal bovine serum (FBS) used was available from Biosera Inc. (France), and the PBS was D-PBS(−) (available from FUJIFILM Wako Pure Chemical Corporation).

$^1$H-NMR analysis of each sample was performed using an ECX500 NMR spectrometer (JEOL). In addition, the FT-IR analysis was performed using a Fourier transform infrared spectrophotometer "IRTracer" (available from Shimadzu Corporation) equipped with a heat-vacuum stirring reflection "Heat Chamber Type-1000° C." (available from ST Japan Inc.).

To summarize the above, configurations of the present disclosure and their variations will be described in addition below.

[1]

A surface-modified nanoparticle including:

a nanocarbon material; and a surface-modifying group of the nanocarbon material, in which the surface-modified nanoparticle has a group containing a boron atom as the surface-modifying group.

[2]

The surface-modified nanoparticle according to [1], in which the nanocarbon material is at least one selected from the group consisting of a nanodiamond, a fullerene, graphene oxide, a nanographite, a carbon nanotube, a carbon nanofilament, an onion-like carbon, a diamond-like carbon, an amorphous carbon, a carbon black, a carbon nanohom, and a carbon nanocoil.

[3]

The surface-modified nanoparticle according to [1] or [2], in which the nanocarbon material is a nanodiamond particle.

[4]

The surface-modified nanoparticle according to any one of [1] to [3], in which the surface-modified nanoparticle has a hydrophilic group and a group containing a boron atom as the surface-modifying groups.

[5]

The surface-modified nanoparticle according to any one of [1] to [4], in which the hydrophilic group is a hydroxyl group, a carboxyl group, a sulfo group, an amino group, and a group containing a hydrophilic polymer chain.

[6]

The surface-modified nanoparticle according to any one of [1] to [5], in which the surface-modified nanoparticle has a group containing a boron atom and a hydrophilic polymer chain as the surface-modifying group.

[7]

The surface-modified nanoparticle according to [5] or [6], in which the hydrophilic polymer chain includes a polyether chain and/or a polyglycerol chain.

[8]

The surface-modified nanoparticle according to any one of [5] to [7], wherein the hydrophilic polymer chain includes a polyglycerol chain.

[9]

The surface-modified nanoparticle according to [7] or [8], wherein the polyglycerol chain is a polyglycerol chain represented by Formula (1) below:

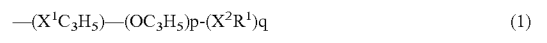

$$—(X^1C_3H_5)—(OC_3H_5)p\text{-}(X^2R^1)q \quad (1)$$

where in Formula (1), p represents an integer of 1 or more, and q represents an integer satisfying q=p+2; $X^1$ represents a divalent group, with a bond extending leftward from $X^1$ in $[X^1C_3H_5]$ being bonded to the nanocarbon material; and $[X^2R^1]$ represents a terminal of the polyglycerol chain; $X^2$ represents a single bond or a divalent group; and $R^1$ represents a hydrogen atom or a monovalent organic group.

[10]

The surface-modified nanoparticle according to [9], in which the $[X^2R^1]$s are identical or different and are OH, $NH_2$, $CH_3$, an alkoxy group, an acyl group, a mono- or di-alkylamino group, a mono- or di-alkenylamino group, an alkylamide group, an alkenylamide group, a quatemary ammonium-substituted alkoxy group, a chlorine-substituted alkoxy group, a polyalkylene oxide group, a cyclic imido group, a carboxyl-substituted alkylamino group, a carboxyl-substituted alkyloxy group, or a group containing a boron atom.

[11]

The surface-modified nanoparticle according to any one of [7] to [10], in which the polyglycerol chain is a polyglycerol chain in which one, some, or all of hydroxyl groups is/are substituted with an amino group(s).

[12]

The surface-modified nanoparticle according to [11], in which at least one or some of the amino group(s) is/are protected by a compound having an acidic functional group.

[13]

The surface-modified nanoparticle according to any one of [5] to [12], in which the boron atom is bonded to the hydrophilic polymer chain via an aromatic ring.

[14]

The surface-modified nanoparticle according to [13], in which the boron atom is directly bonded to the aromatic ring.

[15]

The surface-modified nanoparticle according to [13] or [14], in which the aromatic ring is bonded to the hydrophilic polymer chain via an alkyleneoxy group or an alkyleneamino group bonded to a carbon atom constituting the aromatic ring.

[16]

The surface-modified nanoparticle according to [15], in which the aspect in which the aromatic ring is bonded to the hydrophilic polymer chain via an alkyleneoxy group or an alkyleneamino group bonded to a carbon atom constituting the aromatic ring is represented by a group represented by Formula (2), where Ar represents an aromatic ring, and $R^3$ represents a substituent that the aromatic ring may have (e.g., a halogen atom, such as a fluorine atom, a chlorine atom, a bromine atom, or an iodine atom; a hydroxyl group; a mercapto group; a carboxy group; an amino group; or an oxo group) and is, for example, preferably an electron-withdrawing group; m is an integer of 0 or more; $R^4$ is a group containing a boron atom, in which the boron atom is directly bonded to a carbon atom constituting the aromatic ring; n is an integer of 1 or more; $R^5$ represents an alkylene group and is a group identical to the alkylene group in the alkyleneoxy group and the alkyleneamino group; Y is an oxygen atom, NH, or $NR^6$; $R^6$ is a monovalent organic group; and the bond extending leftward from Y is bonded to a hydrophilic polymer chain (preferably a polyglycerol chain).

[17]

The surface-modified nanoparticle according to [16], in which the boron atom and the alkyleneoxy group or the alkyleneamino group are each bonded to carbon atoms adjacent to each other among carbon atoms constituting the aromatic ring.

[18]

The surface-modified nanoparticle according to [17], in which the aspect in which the boron atom and the alkyleneoxy group or the alkyleneamino group are each bonded to carbon atoms adjacent to each other among carbon atoms constituting the aromatic ring is represented by a group represented by Formula (3), where $R^3$, $R^4$, $R^5$, and Y are identical to those described in Formula (2).

[19]

The surface-modified nanoparticle according to any one of [16] to [18], in which the group containing a boron atom in $R^4$ is a group represented by Formula (4) below:

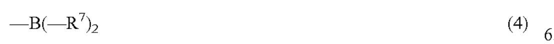

$$—B(—R^7)_2 \quad (4)$$

where in Formula (4), $R^7$s are identical to or different from each other and represent a hydrogen atom, a hydroxyl group, an amino group, a sulfo group, or a monovalent organic group; in addition, two $R^7$s may be bonded to each other to form a ring (hydrocarbon-containing ring); when two $R^7$s are bonded to each other to form a ring, the ring may be formed via an oxygen atom; furthermore, the carbon atoms constituting the ring may form a double bond with an adjacent carbon atom; and the number of carbons constituting the ring is not particularly limited and is, for example, preferably from 4 to 12, more preferably from 4 to 10, and even more preferably from 4 to 6.

[20]

The surface-modified nanoparticle according to any one of [13] to [19], in which the aromatic ring is bonded to the hydrophilic polymer chain via an alkyleneamino group bonded to a carbon atom constituting the aromatic ring, and the amino group in the alkyleneamino group is a tertiary amino group.

[21]

The surface-modified nanoparticle according to any one of [13] to [20], in which the aromatic ring is an aromatic hydrocarbon ring or an aromatic heterocycle.

[22]

The surface-modified nanoparticle according to [21], in which the hydrocarbon ring in the aromatic ring is a $C_{6-14}$ hydrocarbon ring (particularly a $C_6$-10 hydrocarbon ring), such as a benzene ring or a naphthalene ring, and the aromatic heterocyclic ring is a ring having a carbon atom and at least one type of heteroatom (e.g., an oxygen atom, a sulfur atom, or a nitrogen atom) in atoms constituting the ring, and fused rings of these.

[23]

The surface-modified nanoparticle according to any one of [13] to [22], in which the aromatic ring is a benzene ring or a pyridine ring.

[24]

The surface-modified nanoparticle according to any one of [13] to [23], in which the aromatic ring has an electron-withdrawing group as a substituent.

[25]

The surface-modified nanoparticle according to [24], in which the electron-withdrawing group is a fluorine atom.

[26]

The surface-modified nanoparticle according to any one of [1] to [25], in which the boron atom is contained as a boronic acid.

[27]

The surface-modified nanoparticle according to any one of [1] to [26], in which the boron atom is enriched in $^{10}B$.

[28]

The surface-modified nanoparticle according to any one of [1] to [27], in which when 0.5 parts by mass of the surface-modified nanoparticle is blended with 99.5 parts by mass of a PBS (pH 7.4)/FBS (45/55 (v/v)) solution and the solution is stored at 25° C., substantially no aggregate forms within 10 minutes as determined by visual inspection.

[29]

The surface-modified nanoparticle according to any one of [1] to [28], in which content of the boron atom is 0.1 mass % or more, 0.5 mass % or more, 1.0 mass % or more, or 1.5 mass % or more.

[30]

The surface-modified nanoparticle according to any one of [1] to [29], in which a mass ratio of the ND to the surface-modifying group [ND/surface-modifying group of the present disclosure] is from 0.2 to 1.5 or from 0.2 to 1.0.

[31]

The surface-modified nanoparticle according to any one of [1] to [30], having a mean volume particle size (MV) of 200 nm or less, 100 nm or less, or 60 nm or less.

[32]

A composition for use in boron neutron capture therapy, the composition containing the surface-modified nanoparticle described in any one of [1] to [31].

INDUSTRIAL APPLICABILITY

The surface-modified nanoparticle of the present disclosure can be easily produced, selectively deliver boron atoms into cancer cells, and also maintain the concentration of boron atoms in the cancer cells. Thus, the surface-modified nanoparticle of the present disclosure can accumulate a sufficient amount of boron atoms in cancer tissues and/or cancer cells, and thus can effectively kill cancer tissues and/or cancer cells by boron neutron capture therapy (BNCT).

The invention claimed is:

1. A surface-modified nanoparticle comprising:

a nanocarbon material; and a surface-modifying group of the nanocarbon material, wherein the surface-modified nanoparticle comprises a group containing a boron atom and a hydrophilic polymer chain as the surface-modifying group, wherein the hydrophilic polymer chain is a polyglycerol chain;

the nanocarbon material comprises a nanodiamond particle, and a mass ratio of the nanodiamond particle [ND] to the surface-modifying group [ND/surface-modifying group] in the surface-modified nanoparticle is from 0.2 to 1.5.

2. The surface-modified nanoparticle according to claim 1, wherein the polyglycerol chain is a polyglycerol chain in which one, some, or all of hydroxyl groups is/are replaced by an amino group(s).

3. The surface-modified nanoparticle according to claim 2, wherein at least one or some of the amino group(s) is/are protected by a compound comprising an acidic functional group.

4. The surface-modified nanoparticle according to claim 1, wherein the boron atom is bonded to the hydrophilic polymer chain via an aromatic ring.

5. The surface-modified nanoparticle according to claim 4, wherein the boron atom is directly bonded to the aromatic ring.

6. The surface-modified nanoparticle according to claim 4, wherein the aromatic ring is bonded to the hydrophilic polymer chain via an alkyleneoxy group or an alkyleneamino group bonded to a carbon atom constituting the aromatic ring.

7. The surface-modified nanoparticle according to claim 6, wherein the boron atom and the alkyleneoxy group or the alkyleneamino group are each bonded to carbon atoms adjacent to each other among carbon atoms constituting the aromatic ring.

8. The surface-modified nanoparticle according to claim 7, wherein the aromatic ring is bonded to the hydrophilic polymer chain via an alkyleneamino group bonded to a carbon atom constituting the aromatic ring, and the amino group in the alkyleneamino group is a tertiary amino group.

9. The surface-modified nanoparticle according to claim 4, wherein the aromatic ring is a benzene ring or a pyridine ring.

10. The surface-modified nanoparticle according to claim 4, wherein the aromatic ring comprises an electron-withdrawing group as a substituent.

11. The surface-modified nanoparticle according to claim 10, wherein the electron-withdrawing group is a fluorine atom.

12. The surface-modified nanoparticle according to claim 1, wherein the boron atom is contained as a boronic acid.

13. The surface-modified nanoparticle according to claim 1, wherein the boron atom is enriched in $^{10}B$.

14. The surface-modified nanoparticle according to claim 1, wherein when 0.5 parts by mass of the surface-modified nanoparticle is blended with 99.5 parts by mass of a PBS (pH 7.4)/FBS (45/55 (v/v)) solution and the solution is stored at 25° C., substantially no aggregate forms within 10 minutes as determined by visual inspection.

15. A composition for use in boron neutron capture therapy, the composition comprising the surface-modified nanoparticle described in claim 1.

* * * * *